United States Patent
Ku

(10) Patent No.: US 11,484,334 B2
(45) Date of Patent: Nov. 1, 2022

(54) CIRCUMCISION APPARATUS, SURGICAL SCISSORS AND CIRCUMCISION METHOD

(71) Applicant: Hsiao-Yuan Ku, Taoyuan (TW)

(72) Inventor: Hsiao-Yuan Ku, Taoyuan (TW)

( * ) Notice: Subject to any disclaimer, the term of this patent is extended or adjusted under 35 U.S.C. 154(b) by 509 days.

(21) Appl. No.: 16/449,360

(22) Filed: Jun. 22, 2019

(65) Prior Publication Data

US 2019/0388116 A1    Dec. 26, 2019

Related U.S. Application Data

(60) Provisional application No. 62/688,473, filed on Jun. 22, 2018.

(51) Int. Cl.
*A61B 17/326* (2006.01)
*A61B 17/3201* (2006.01)

(52) U.S. Cl.
CPC ........ *A61B 17/326* (2013.01); *A61B 17/3201* (2013.01)

(58) Field of Classification Search
CPC . A61B 17/326; A61B 17/3201; A61B 17/122; A61B 17/1222; A61B 17/128; A61B 2017/00353; A61B 2017/00876
See application file for complete search history.

(56) References Cited

U.S. PATENT DOCUMENTS

| | | | | |
|---|---|---|---|---|
| 4,452,357 A | * | 6/1984 | Klieman | A61B 17/0682 606/143 |
| 5,462,555 A | * | 10/1995 | Bolanos | A61B 17/122 606/151 |
| 6,217,590 B1 | * | 4/2001 | Levinson | A61B 17/1285 606/139 |
| 2002/0177859 A1 | * | 11/2002 | Monassevitch | A61B 17/128 606/139 |
| 2015/0359538 A1 | * | 12/2015 | Yeatts, II | A61B 17/122 606/120 |
| 2016/0213377 A1 | * | 7/2016 | Shankarsetty | A61B 17/1285 |
| 2019/0262029 A1 | * | 8/2019 | Messerly | A61B 17/00491 |

* cited by examiner

*Primary Examiner* — Ashley L Fishback

(57) ABSTRACT

A circumcision apparatus is provided. The circumcision apparatus includes a first surgical scissors and a second surgical scissors. The first surgical scissors include two first clips and one pair of blades, and the second surgical scissors include one second clip and one pair of blades. In the circumcision operation, after the foreskin is cut by the first surgical scissors along the direction of the shaft of the penis, the two first clips clamp a part of the foreskin near a first incision. After the foreskin is cut further by the second surgical scissors along the circumference of the penis, the second clip clamps another part of the foreskin near a second incision. Therefore, bleeding from the first and second incisions can be effectively reduced.

12 Claims, 23 Drawing Sheets

US 11,484,334 B2

CIRCUMCISION APPARATUS, SURGICAL SCISSORS AND CIRCUMCISION METHOD

CROSS REFERENCE TO RELATED APPLICATIONS

This application claims the benefit of U.S. Provisional Application No. 62/688,473, filed Jun. 22, 2018, the entirety of which is incorporated by reference herein.

BACKGROUND OF THE DISCLOSURE

Field of the Disclosure

The present disclosure relates to a circumcision apparatus, and in particular it relates to a circumcision apparatus capable of effectively reducing operating time.

Description of the Related Art

Male circumcision is one of the most common surgical procedures in the world. Circumcision is a surgical operation for exposing the glans by removing an appropriate length of foreskin; that is, the foreskin covering the glans. Circumcision is performed for a variety of reasons, such as religious rituals or for disease prevention. A human male may receive a circumcision at some point in his life. For example, circumcision has traditionally been performed either immediately after birth, during childhood, during adolescence, or occasionally on a young adult.

One conventional method for performing circumcision is by surgically removing the foreskin after physically pulling the foreskin over the glans. However, using this surgical method to remove the foreskin usually causes bleeding because the removed foreskin is live tissue. Such methods may involve hemostasis and a relatively long period of healing at the point of the incision. For example, the healing period may last a few weeks, and the patient has to tolerate pain for a long period of healing. In addition, when such a procedure is performed on adult males, suturing may also be required.

Although existing apparatuses or tools for circumcision have been generally adequate for their intended purposes, they have not been entirely satisfactory in all respects.

BRIEF SUMMARY OF THE DISCLOSURE

Accordingly, one objective of the present disclosure is to provide a circumcision apparatus to solve the above problems.

According to some embodiments of the disclosure, a circumcision apparatus is provided, wherein the circumcision apparatus includes a first surgical scissors, and the first surgical scissors includes a pair of first blades and two first clips. The pair of first blades is configured to cut a foreskin along a direction of a shaft of a penis. The two first clips are configured to clamp the foreskin near a first incision in response to the foreskin being cut by the first surgical scissors, resulting in the first incision.

According to some embodiments, the first surgical scissors further includes a left part and a right part. The left part has two side grooves and a central groove. The central groove is disposed between the side grooves of the left part. The right part is joined to the left part and has two side grooves and a central groove. The central groove is disposed between the two side grooves of the right part. The central groove of the left part and the central groove of the right part are configured to respectively accommodate the pair of first blades, and the two side grooves of the left part and the two side grooves of the right part are configured to receive the two first clips, wherein each of the first clips has a V-shaped structure.

According to some embodiments, a height of the first clip in a first direction is greater than a height of the first blade in the first direction.

According to some embodiments, the circumcision apparatus further comprises a clip holder, and the clip holder has a triangular prism structure corresponding to a shape of the first clip.

According to some embodiments, the circumcision apparatus further includes a second surgical scissors, and the second surgical scissors includes: a pair of second blades and a second clip. The pair of second blades is configured to cut the foreskin along a circumference of the penis. The second clip is configured to clamp the foreskin near a second incision in response to the foreskin being cut by the second surgical scissors, resulting in the second incision.

According to some embodiments, the second surgical scissors further includes a left part and a right part. The left part has a first groove and a second groove. The right part is joined to the left part and has a first groove and a second groove. The first groove of the left part and the first groove of the right part are configured to respectively accommodate the pair of second blades, and the second groove of the left part and the second groove of the right part are configured to receive the second clip.

According to some embodiments, a height of the second clip in a first direction is greater than a height of the second blade in the first direction.

According to some embodiments, the left part of the second scissors has a curved scissoring portion on which the first groove of the left part is formed, and the right part of the second scissors has a curved scissoring portion on which the first groove of the right part is formed.

According to some embodiments, the second clip has a curved-shaped structure corresponding to the two second grooves.

According to some embodiments, each of the first clip and the second clip includes a first portion and a second portion. A protrusion is formed on an end of the first portion. A slot is formed on an end of the second portion. A shape of the protrusion matches a shape of the slot so that the protrusion is configured to be securely engaged with the slot.

According to some embodiments, the first surgical scissors further includes a left part, a right part and a middle part. The left part has two side grooves and a gap. The gap is disposed between the two side grooves of the left part. The right part has two side grooves and a central groove. The central groove is disposed between the two side grooves of the right part. The middle part is joined to the left part and the right part on a middle point and is sandwiched between the left part and the right part. The middle part is configured to rotate around the middle point relative to the right part and the left part. The two side grooves of the left part and the two side grooves of the right part are configured to receive the two first clips, the central groove of the right part is configured to accommodate one of the pair of first blades, and the middle part includes the other one of the pair of blades.

According to some embodiments, the left part further has a handle portion, the right part further has a handle portion, and the first surgical scissors further includes a guiding part which is connected between the handle portion of the left part and the handle portion of the right part.

According to some embodiments, the guiding part is affixed to the handle portion of the left part and includes a guiding slot, the handle portion of the right part includes a pin disposed inside the guiding slot, so that the handle portion of the right part is configured to move along the guiding slot relative to the handle portion of the left part.

According to some embodiments, the middle part has a handle portion, the first surgical scissors further includes a resilient member which is connected to the handle portion of the middle part and the handle portion of the left part, and the resilient member is configured to provide a resilient force to drive the handle portion of the middle part away from the handle portion of the left part.

According to some embodiments, the left part further includes a scissoring portion, and the first blade of the middle part is constrained when the first blade of the middle part is in contact with an inner wall surface of the scissoring portion of the left part.

According to some embodiments, the circumcision apparatus further includes a clip holder, and the clip holder includes a middle portion and two side portions. The middle portion has two grooves for receiving two first clips. Each of the side portions has a slot, and the slots are configured to accommodate and constrain the left part and the right part.

According to some embodiments, one of the side portions includes a narrow slot which is configured to receive the first blade of the middle part.

A surgical scissors includes a left part, a right part, a middle part and a pair of blades. The left part has two side grooves and a gap. The gap is disposed between the two side grooves of the left part. The right part has two side grooves and a central groove. The central groove is disposed between the two side grooves of the right part. The middle part is joined to the left part and the right part on a middle point and is sandwiched between the left part and the right part. The middle part is configured to rotate around the middle point relative to the right part and the left part. The pair of blades is configured to cut a foreskin of a penis. The two side grooves of the left part and the two side grooves of the right part are configured to receive two clips, the central groove of the right part is configured to accommodate one of a pair of blades, and the middle part includes the other one of the pair of blades.

A circumcision method includes: cutting a foreskin along one side of a section of the foreskin by a first surgical scissors, resulting in a first incision; clamping the foreskin on two sides of the first incision by two clips, wherein the two clips are disposed on the first surgical scissors; cutting the foreskin along another side of the section of the foreskin by the first surgical scissors, resulting in a second incision; clamping the foreskin on two sides of the second incision by another two clips, wherein the another two clips are disposed on the first surgical scissors; cutting the foreskin along a boundary line of the foreskin by a second surgical scissors, resulting in a third incision; and clamping the foreskin by a second clip near the third incision, wherein the second clip is disposed on the second surgical scissors.

According to some embodiments, the circumcision method further includes: moving the first surgical scissors to a clip holder to engage other first clips on the first surgical scissors.

The disclosure provides a circumcision apparatus, including at least one first surgical scissors and at least one second surgical scissors. The first surgical scissors includes a pair of blades and two clips, and the second surgical scissors includes a pair of blades and one clip. The surgeon can use the first surgical scissors to cut the foreskin along the direction of the penis of the patient, and then can use the second surgical scissors to remove a part of foreskin. Because the clips clamp the foreskin before the blades cut the foreskin, bleeding from the incision can be effectively reduced in the procedure of the circumcision surgery.

In addition, after the surgery is finished, the clips remain on the foreskin. After one or two weeks, the clips and the necrotic foreskin (a small part of foreskin) are separated from the healthy foreskin by themselves, and sutures or stitches are not required, so that the patient's daily life will not be affected. Moreover, the surgeon can use a third surgical scissors instead of the second surgical scissors, and a part of the foreskin can be cut off more smoothly. Therefore, the incision is trimmed to be straighter, and the incision of the foreskin will heal faster.

Furthermore, in some embodiments, the surgeon can also use the surgical scissors to perform circumcision, and the foreskin can be cut more smoothly and completely by the surgical scissors, resulting in a very straight incision, to help the incision of the foreskin to be healed faster. Consequently, by utilizing the surgical scissors of the present disclosure mentioned above, the procedures of cutting, hemostasis and suturing can be completed at once, so as to significantly reduce operating time in contrast to the conventional circumcision operation.

Additional features and advantages of the disclosure will be set forth in the description which follows, and, in part, will be obvious from the description, or can be learned by practice of the principles disclosed herein. The features and advantages of the disclosure can be realized and obtained by means of the instruments and combinations pointed out in the appended claims. These and other features of the disclosure will become more fully apparent from the following description and appended claims, or can be learned by the practice of the principles set forth herein.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION OF THE ILLUSTRATIVE EMBODIMENTS

Figure 1:
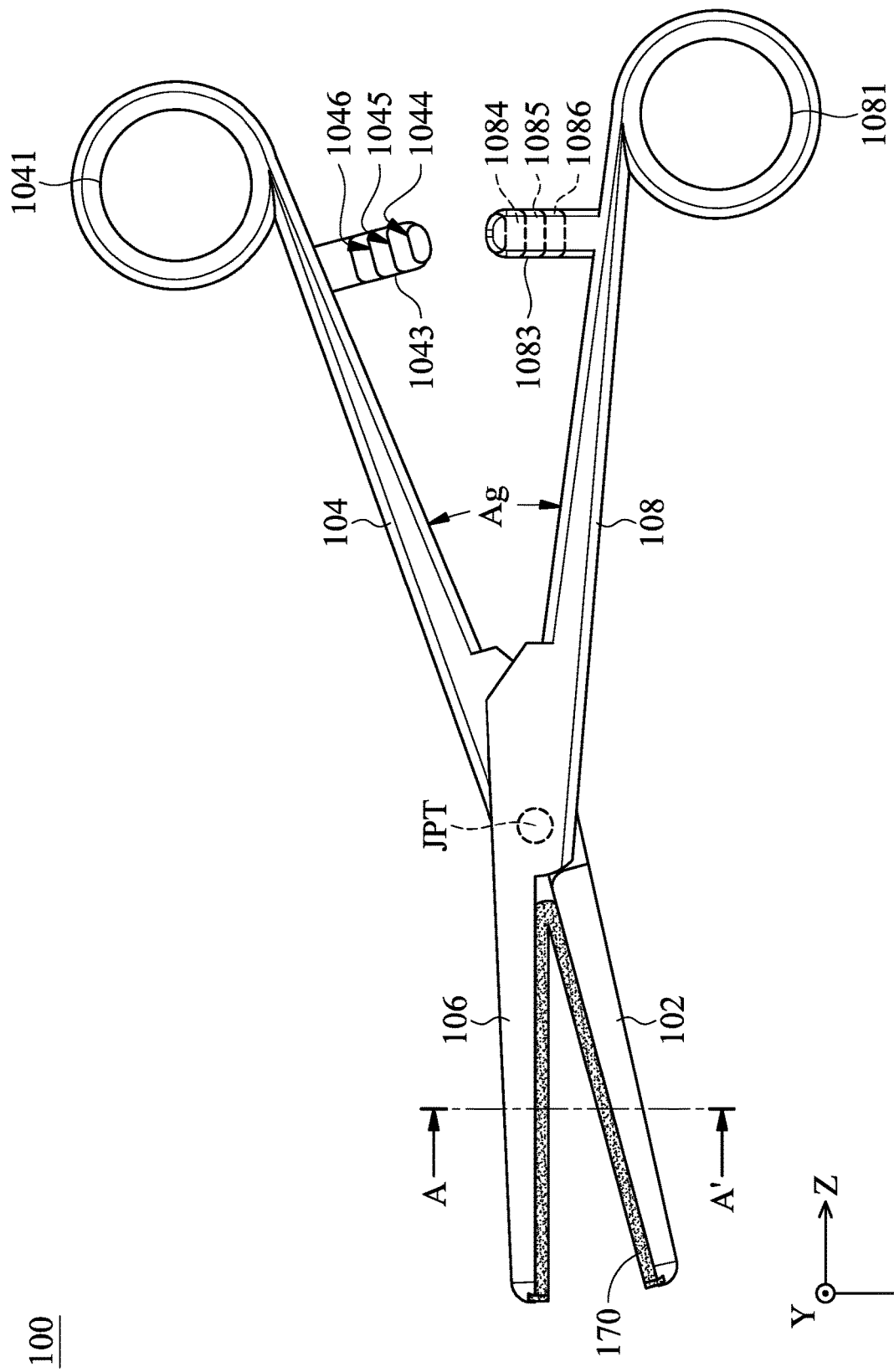
FIG. 1 shows a top view diagram of a pair of first surgical scissors according to some embodiments of the present disclosure.

The following disclosure provides many different embodiments, or examples, for implementing different features of the subject matter provided. Specific examples of solutions and arrangements are described below to simplify the present disclosure. These are, of course, merely examples and are not intended to be limiting. For example, the formation of a first feature over or on a second feature in the description that follows may include embodiments in which the first and the second features are formed in direct contact, and may also include embodiments in which additional features may be formed between the first and the second features, such that the first and the second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Furthermore, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. It should be understood that additional operations can be provided before, during, and after the method, and some of the operations described can be replaced or eliminated for other embodiments of the method.

In addition, the terms "first", "second", "third", "fourth", and the like are merely generic identifiers and, as such, may be interchanged in various embodiments. For example, while an element may be referred to as a "first" element in some embodiments, the element may be referred to as a "second" element in other embodiments.

Circumcision is a common and safe surgical operation. In a conventional circumcision procedure, the patient is brought to an operating room, and a satisfactory general anesthesia is induced. For example, a penile block is done using a 50% mixture of 1% lidocaine and 0.25% Marcaine. After that, a surgeon utilizes many pairs of surgical scissors and clamps to excise and trim the redundant foreskin which covers the glans. Bleeding from the incisions is inevitable and a lot of bleeding points need to be controlled by electrocoagulation, so that hemostasis is established. The cut margin of penile skin was approximated with multiple interrupted 5-0 chromic sutures. However, the circumcision procedure takes time (over 30 minutes) and needs a lot of clamps to establish the hemostasis.

Figure 2:
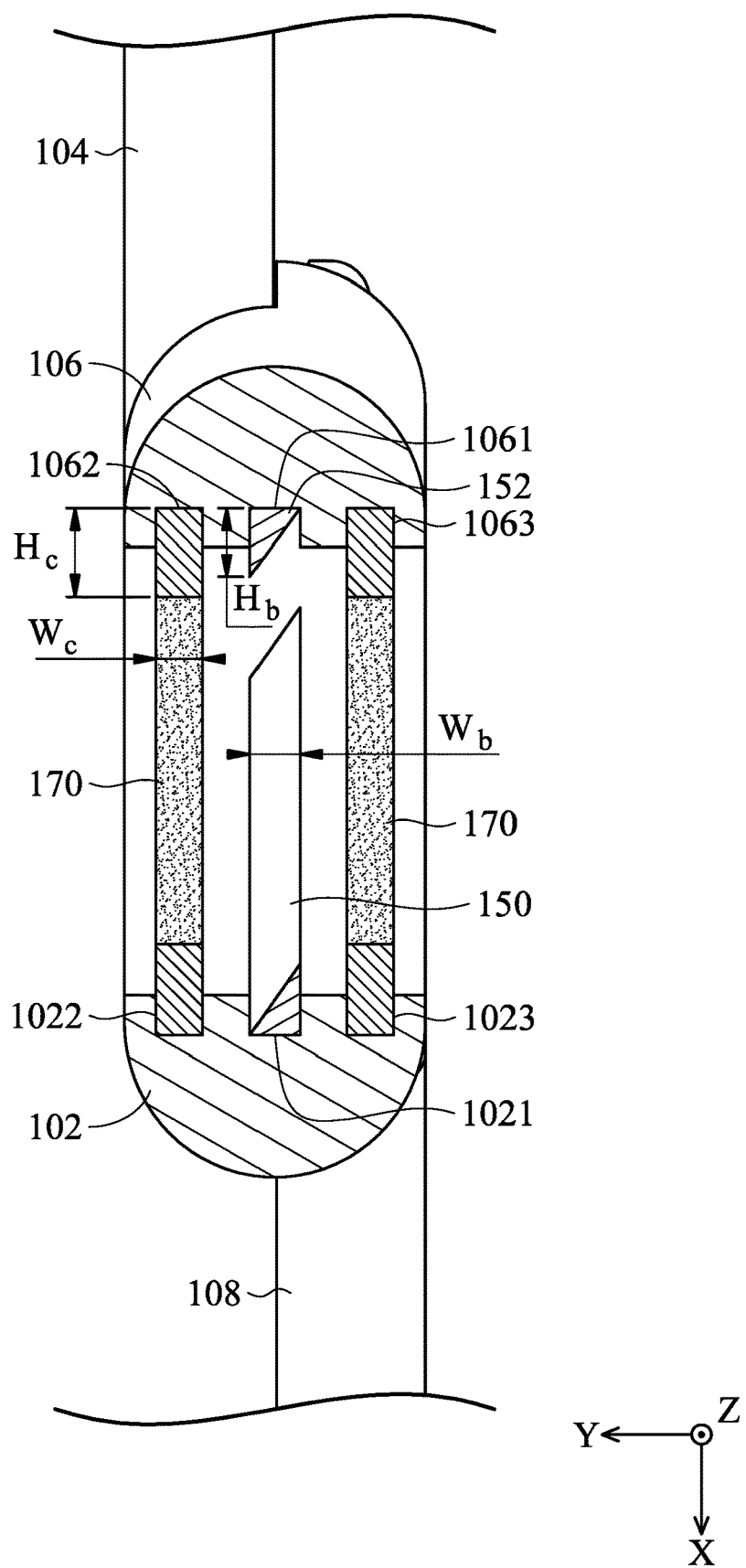
FIG. 2 show a sectional view along line A-A' in FIG. 1 according to the embodiment of the disclosure.
Figure 3:
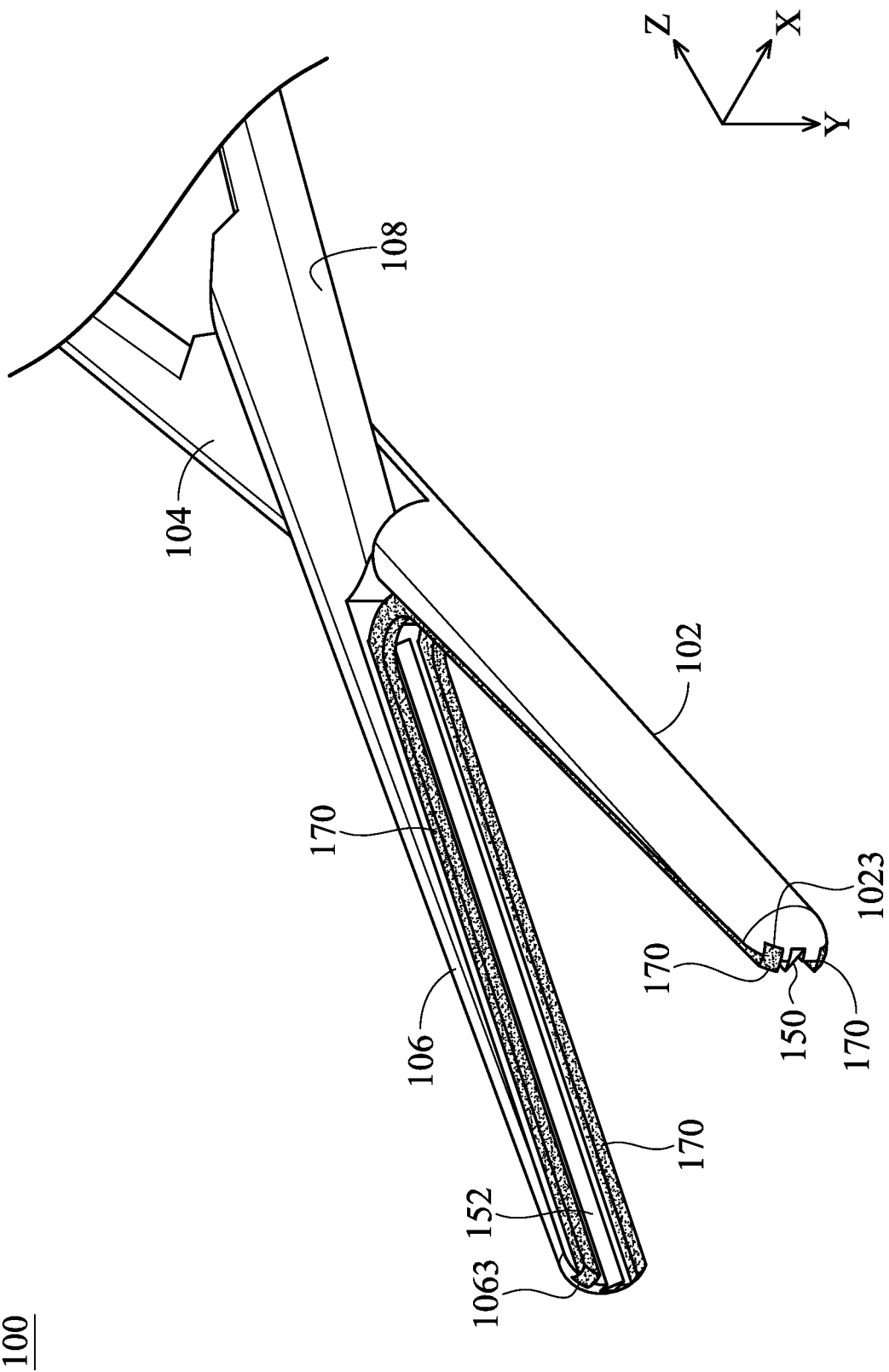
FIG. 3 shows a partial structural diagram of the pair of first surgical scissors according to the embodiment of the present disclosure.

The present disclosure provides a circumcision apparatus for circumcision operation. In some embodiments, the circumcision apparatus can include at least one first surgical scissors and at least one second surgical scissors. Please refer to FIG. 1 to FIG. 3. FIG. 1 shows a top view diagram of a pair of first surgical scissors 100 according to some embodiments of the present disclosure. FIG. 2 show a sectional view along line A-A' in FIG. 1 according to the embodiment of the disclosure. FIG. 3 shows a partial structural diagram of the pair of first surgical scissors 100 according to the embodiment of the present disclosure. As shown in FIG. 1, the first surgical scissors 100 includes a left part and a right part, and the left part and the right part are joined on a middle point JPT. In this embodiment, the left part and the right part are made of stainless steel, but they are not limited thereto. The left part includes a scissoring portion 102 and a handle portion 104, and the right part includes a scissoring portion 106 and a handle portion 108.

There is a hole 1041 formed at the bottom of the handle portion 104, and there is a hole 1081 formed at the bottom of the handle portion 108, so that fingers of a surgeon can put through the holes 1041 and 1081 to use the first surgical scissors 100. In addition, as shown in FIG. 1, the handle portion 108 further includes a first engaging portion 1083, and the handle portion 104 further includes a second engaging portion 1043. In particular, there are three protrusions 1084, 1085 and 1086 formed on the first engaging portion 1083, and there are three grooves 1044, 1045 and 1046 formed on the second engaging portion 1043. The protrusions 1084, 1085 and 1086 respectively correspond to the grooves 1044, 1045 and 1046, and the protrusions 1084, 1085 and 1086 are protruded along the Y-axis direction in this embodiment.

When the handle portion 104 and the handle portion 108 are forced to be close to each other, at least one of the protrusions is engaged with the corresponding grooves. For example, the groove 1044 can be only engaged with the protrusion 1084, or the groove 1044 and the groove 1045 are respectively engaged with the protrusion 1084 and protrusion 1085, so that the handle portion 108 and the handle portion 104 can be fixed at two different angles. In addition, when the first surgical scissors 100 is closed, the grooves 1044, 1045 and 1046 are all engaged with the protrusions 1084, 1085 and 1086, and an included angle Ag between the handle portion 104 and the handle portion 108 is about 0 degrees.

Next, please refer to FIG. 1 to FIG. 3 together. As shown in FIG. 2, there are three long-strip grooves 1061, 1062 and 1063 formed on the scissoring portion 106, and there are three long-strip grooves 1021, 1022 and 1023 formed on the scissoring portion 102. The long-strip groove 1061 is disposed between the long-strip grooves 1062 and 1063 (the side grooves). The long-strip groove 1021 is disposed between the long-strip grooves 1022 and 1023 (the side grooves). The long-strip grooves 1061 and 1021 (the central grooves) are configured to accommodate a pair of first blades (a blade 152 and a blade 150) respectively. In this embodiment, the blades 150 and 152 can respectively be detachably installed in the long-strip grooves 1021 and 1061, but they are not limited thereto. For example, in other embodiments, the blade 152 and the scissoring portion 106 are integrally formed in one piece, and the blade 150 and the scissoring portion 102 are integrally formed in one piece. In addition, in some embodiments, the first surgical scissors 100, the blade 150 and the blade 152 are disposable and can be made of plastic steel.

As shown in FIG. 2 and FIG. 3, the long-strip grooves 1022 and 1062 are configured to receive a clip 170 (the first clip), and the long-strip grooves 1023 and 1063 are configured to receive another clip 170 (another first clip). Each of the clips 170 has a V-shaped structure, and the size of each of the clips can be the same. The clip 170 can be detachably installed in the long-strip grooves 1022 and 1062, and another clip 170 can be detachably installed in the long-strip grooves 1023 and 1063, as shown in FIG. 3. In this embodiment, the two clips 170 are made of stainless steel or Ni—Al alloys.

As shown in FIG. 2, the blade 150 is perpendicular to the XY plane, and has a height Hb along the X-axis direction, and each of the clips 170 has a height He along the X-axis direction (a first direction). In addition, the blade 150 or the blade 152 has a width Wb along the Y-axis direction, and each of the clips 170 has a width We along the Y-axis direction. In this embodiment, the width We is equal to the width Wb, but the width We can be different from the width Wb in other embodiments.

In addition, it should be noted that the depths of long-strip grooves 1061, 1062 and 1063 are the same, and the height He is greater than the height Hb along the X-axis direction. Similarly, the depths of the long-strip grooves 1021, 1022 and 1023 are the same. Based on this structural design, when a surgeon uses the first surgical scissors 100 to trim the foreskin of a patient, the two clips 170 clamp the foreskin prior to the blade 150 and the blade 152 cutting the foreskin. As a result, the two clips 170 can clamp two sides of the incision result from the blade 150 and the blade 152, and bleeding from the incision can be reduced.

Figure 4:
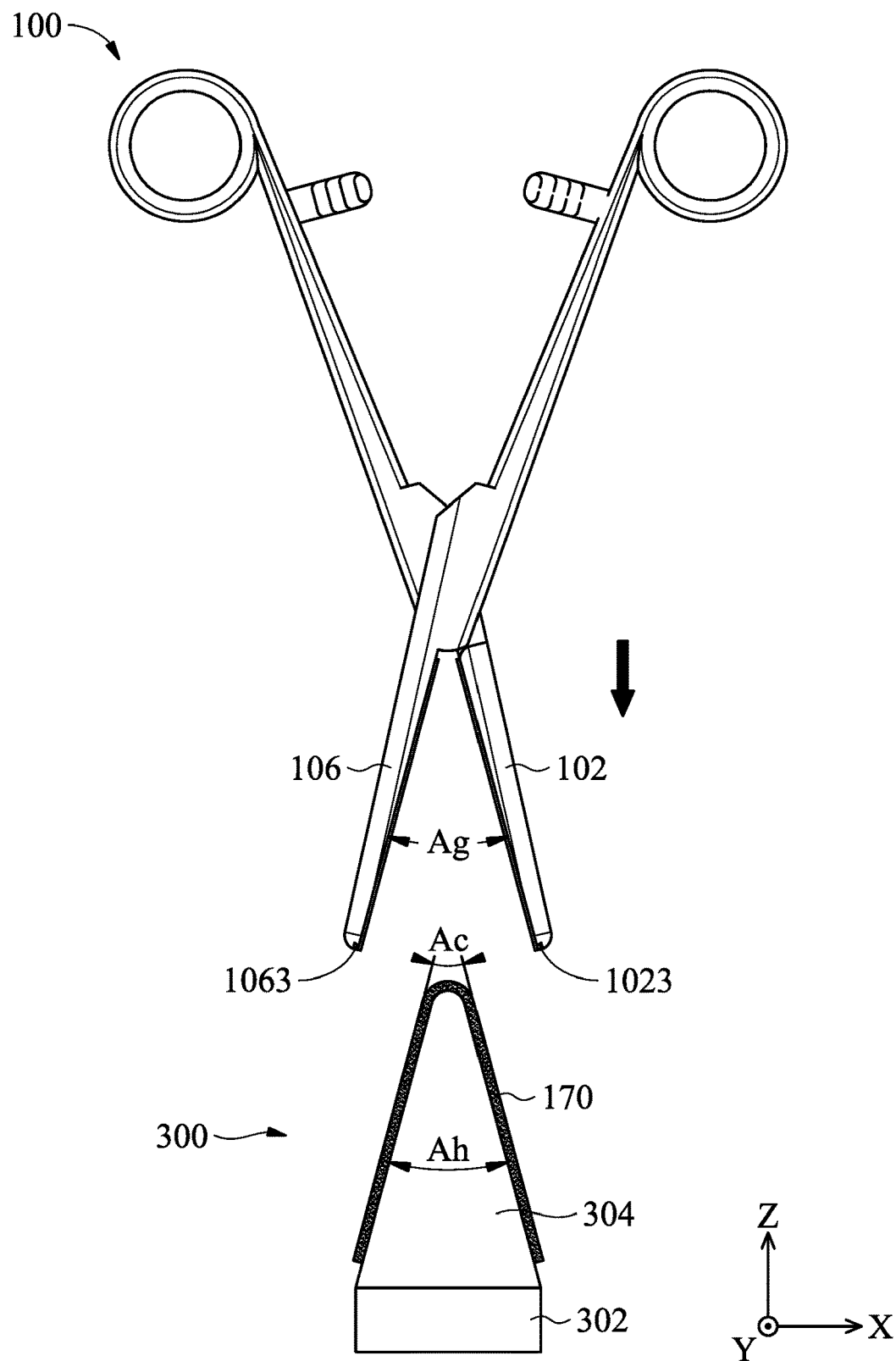
FIG. 4 shows a front view of a clip holder and the first surgical scissors according to some embodiments of the present disclosure.
Figure 5:
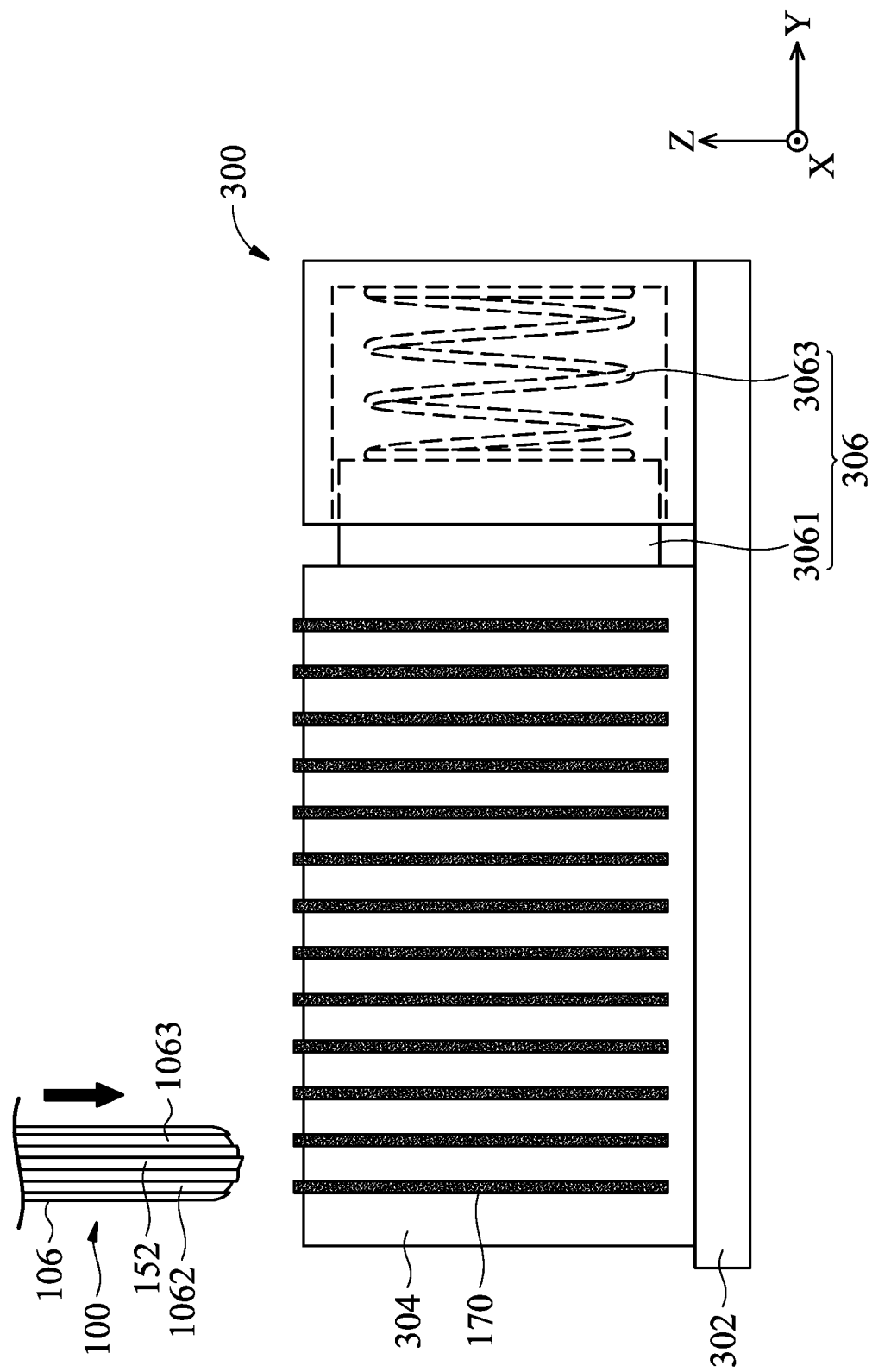
FIG. 5 shows a side view of the clip holder according to some embodiments of the present disclosure.

Please refer to FIG. 4 and FIG. 5. FIG. 4 shows a front view of a clip holder 300 and the first surgical scissors 100 according to some embodiments of the present disclosure. FIG. 5 shows a side view of the clip holder 300 according to some embodiments of the present disclosure. As shown in FIG. 4 and FIG. 5, the clip holder 300 includes a base 302 and a holding structure 304. The holding structure 304 is connected to the base 302 and has a triangular prism structure, which corresponds to the shape of the clip 170, so that a plurality of the clips 170 can be held on the holding structure 304. In this embodiment, the clip holder 300 can hold thirteen clips 170, but the number of clips 170 can be more or less in another embodiment.

As shown in FIG. 4, the surgeon can open the first surgical scissors 100 and move the first surgical scissors 100 toward the clip holder 300 along the direction indicated by the arrow (−Z-axis direction), and the scissoring portion 102 and the scissoring portion 106 are in contact with the clip 170, so that one clip 170 can be engaged in the long-strip grooves 1022 and 1062, and another clip 170 can be engaged in the long-strip grooves 1023 and 1063.

In addition, the clip 170 has an included angle Ac, the holding structure 304 has an included angle Ah, and the included angle Ac is substantially equal to the included angle Ah. It should be noted that the clip 170 also has an elastic force which keeps the angle Ac not being less than the included angle Ah. Therefore, when the included angle Ag is less than the included angle Ac, the elastic force can help the clip 170 to be securely engaged in the long-strip grooves 1022 and 1062 or in the long-strip grooves 1023 and 1063.

Furthermore, the first surgical scissors 100 can be made of stainless steel with magnetism, and the clips 170 are made of stainless steel or Ni—Al alloys with magnetism. Therefore, a magnetic attraction force can be generated by the first surgical scissors 100 and the clip 170, so that when the first surgical scissors 100 moves close to the clip holder 300, the clip 170 can be attracted and be securely engaged in the long-strip grooves 1022 and 1062 or the long-strip grooves 1023 and 1063. Moreover, the magnetic attraction force can prevent the clip 170 from separating from the first surgical scissors 100, so as to increase the safety of the circumcision surgery.

In addition, as shown in FIG. 5, the clip holder 300 can further include a pushing mechanism 306, and the pushing mechanism 306 is configured to push the holding structure 304 to move relative to the base 302. For example, in this embodiment, the pushing mechanism 306 can include a pushing pad 3061 and a spring 3063. The spring 3063 provides a resilient force to drive the pushing pad 3061 to move along the Y-axis direction, so that the pushing pad 3061 can push the holding structure 304 with the clips 170 to move in order, so as to facilitate the surgeon to install the clip 170 on the first surgical scissors 100. The pushing mechanism 306 is not limited to this embodiment. For example, in another embodiment, the pushing mechanism 306 can directly pushes the plurality of clips 170 to move relative the base 302.

Figure 6:
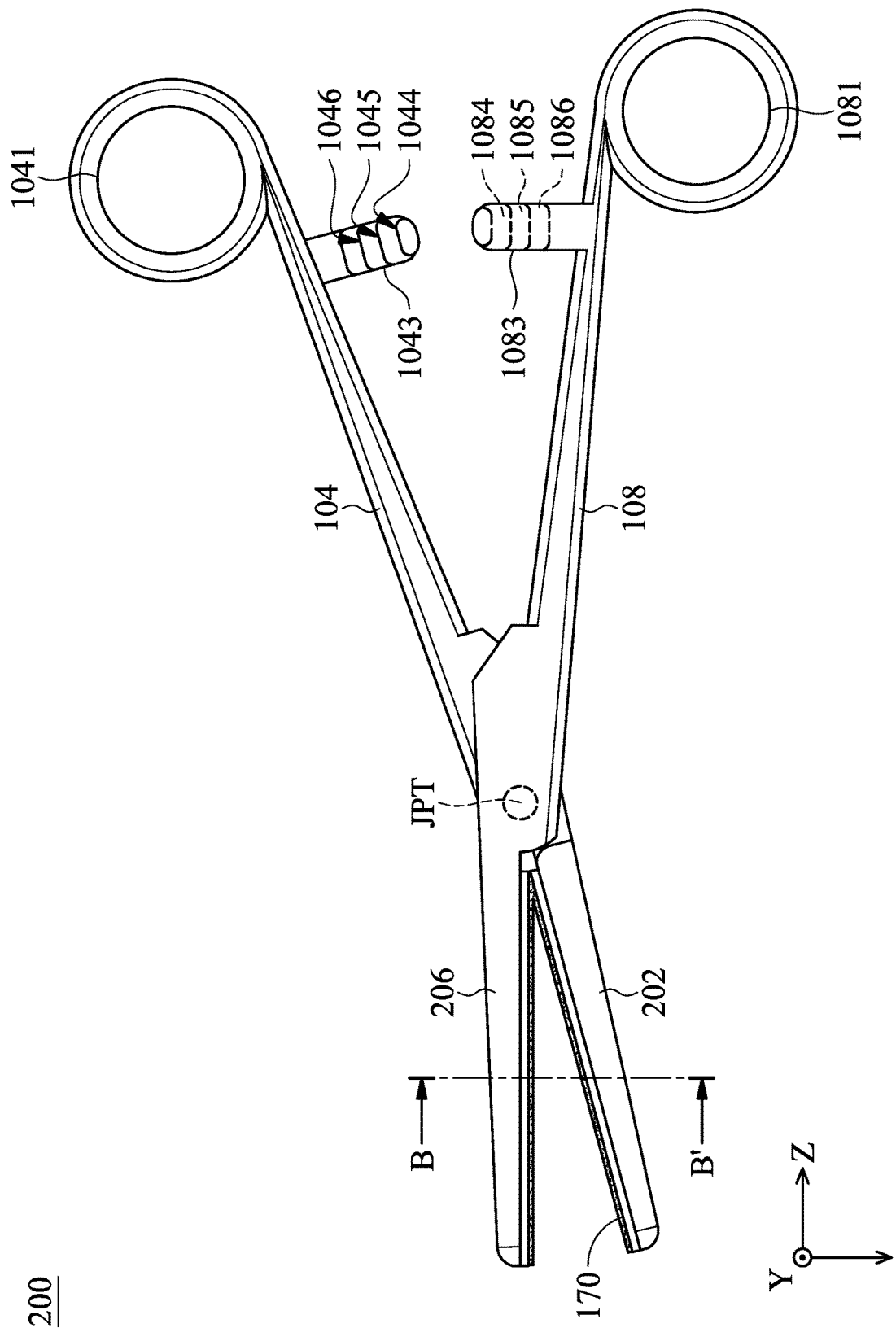
FIG. 6 shows a top view diagram of a pair of second surgical scissors according to some embodiments of the present disclosure.
Figure 7:
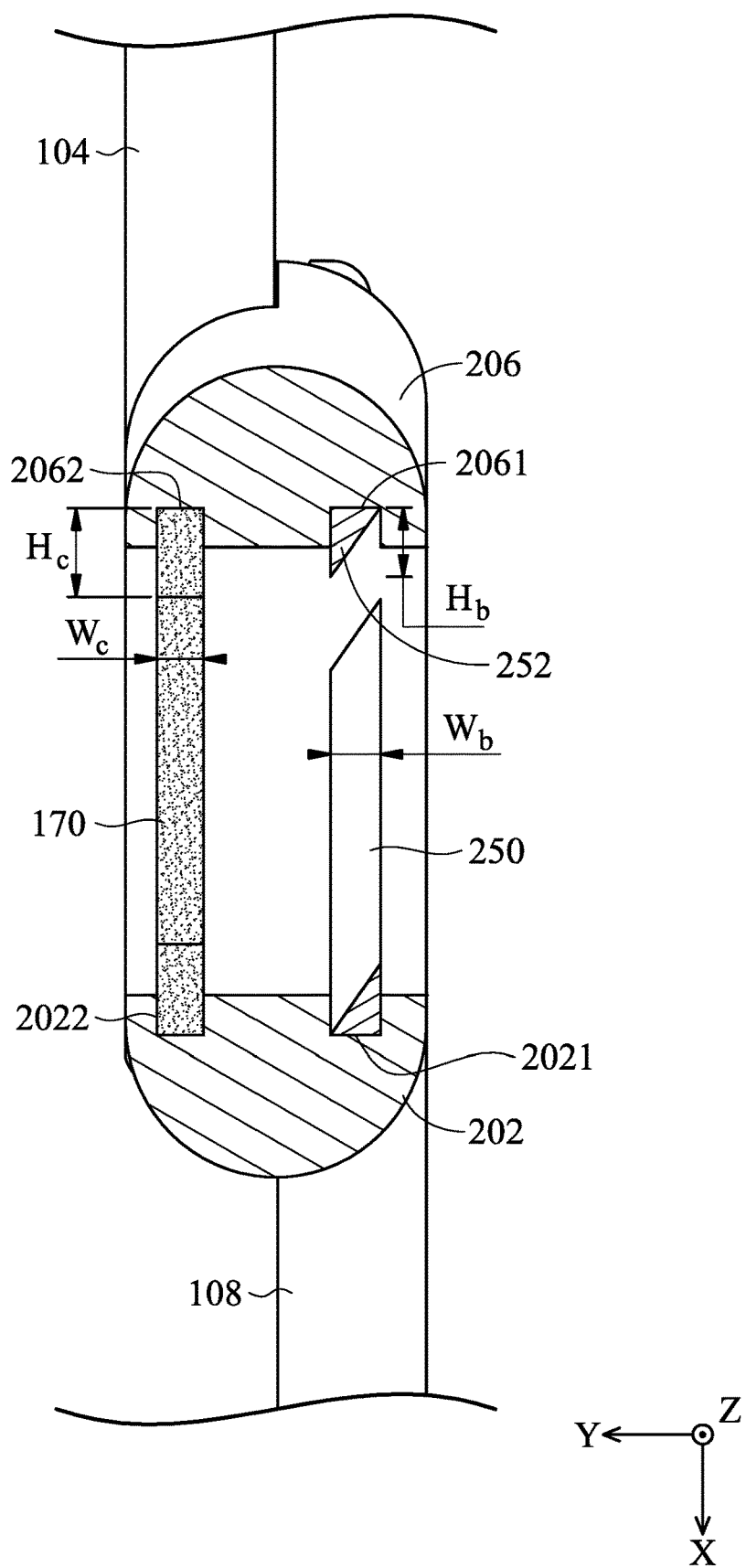
FIG. 7 show a sectional view along line B-B' in FIG. 6 according to the embodiment of the disclosure.
Figure 8:
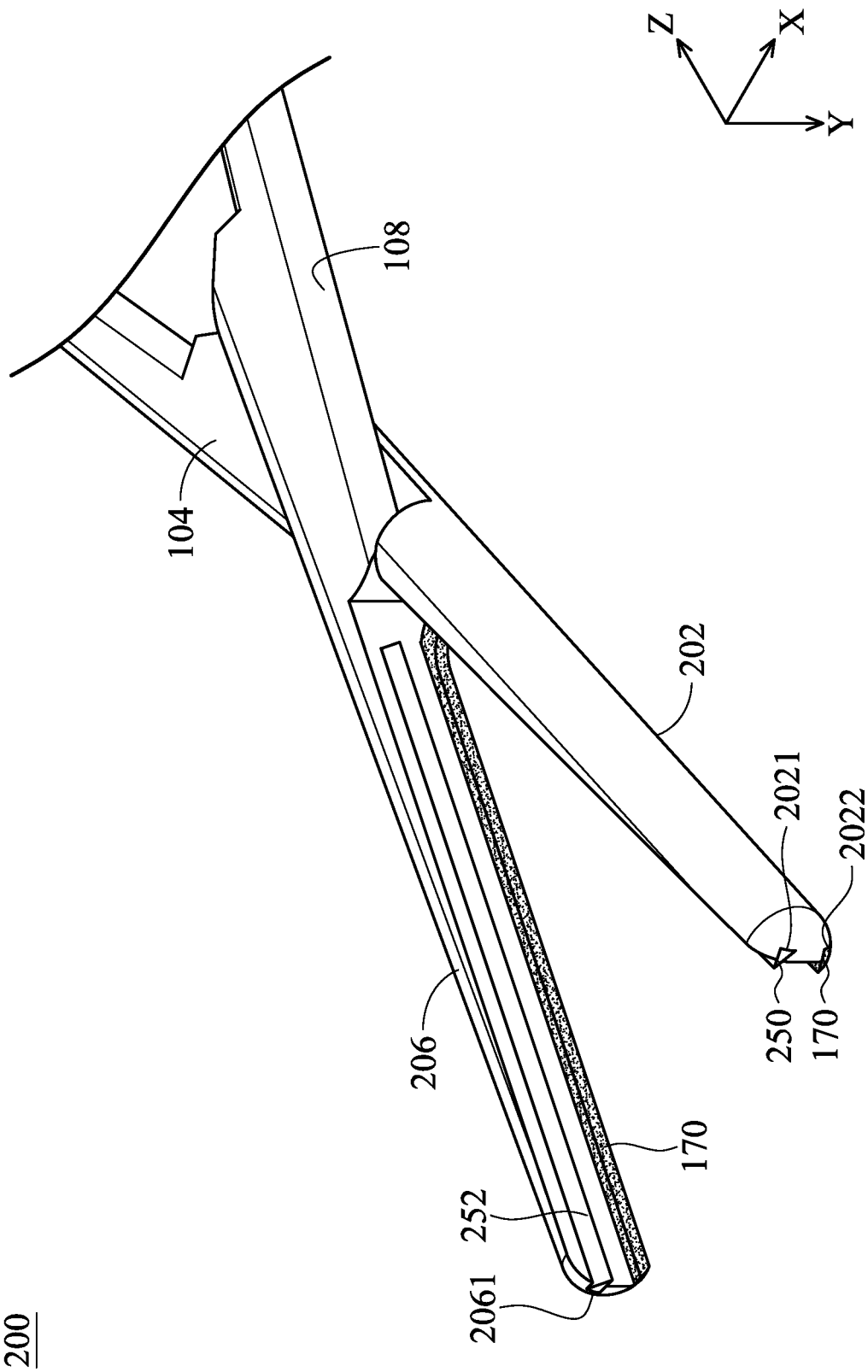
FIG. 8 shows a partial structural diagram of the pair of second surgical scissors according to the embodiment of the present disclosure.

Please refer to FIG. 6 to FIG. 8. FIG. 6 shows a top view diagram of a pair of second surgical scissors 200 according to some embodiments of the present disclosure. FIG. 7 show a sectional view along line B-B' in FIG. 6 according to the embodiment of the disclosure. FIG. 8 shows a partial structural diagram of the pair of second surgical scissors 200 according to the embodiment of the present disclosure. Similar to the first surgical scissors 100, the second surgical scissors 200 also includes a left part and a right part, and the left part and the right part are joined at the middle point JPT. Most structures of the second surgical scissors 200 are similar to the first surgical scissors 100, and the difference between the first surgical scissors 100 and the second surgical scissors 200 is that the second surgical scissors 200 includes a scissoring portion 202 and a scissoring portion 206, and each of the scissoring portion 202 and the scissoring portion 206 includes two grooves.

In this embodiment, as shown in FIG. 7, there are a first groove (the long-strip groove 2061) and a second groove (the long-strip groove 2062) formed on the scissoring portion 206, and there are a first groove (the long-strip groove 2021) and a second groove (the long-strip groove 2022) formed on the scissoring portion 202. The long-strip grooves 2061 and 2021 are configured to accommodate a pair of second blades (a blade 252 and a blade 250) respectively. In this embodiment, the blades 250 and 252 can respectively be detachably installed in the long-strip grooves 2021 and 2061. In other embodiments, the blades 250, 252 and the scissoring portion 202, 206 can be integrally formed. Similarly, the second surgical scissors 200 can be made of stainless steel, or can be made of plastic steel.

As shown in FIG. 7 and FIG. 8, the long-strip grooves 2022 and 2062 are configured to receive a clip 170 (the second clip). In addition, the blade 252 has a height Hb along the X-axis direction, and the clip 170 has a height He along the X-axis direction. It should be noted that the depths of long-strip grooves 2061 and 2062 are the same, and the height He is greater than the height Hb along the X-axis direction so that when the surgeon uses the second surgical scissors 200 to trim the foreskin of the patient, the clip 170 clamps the foreskin prior to the blade 250 and the blade 252 cutting the foreskin. Similarly, the clip 170 can clamp a part of foreskin near the incision result from the blade 250 and the blade 252, and bleeding at the incision can also be reduced.

Figure 9:
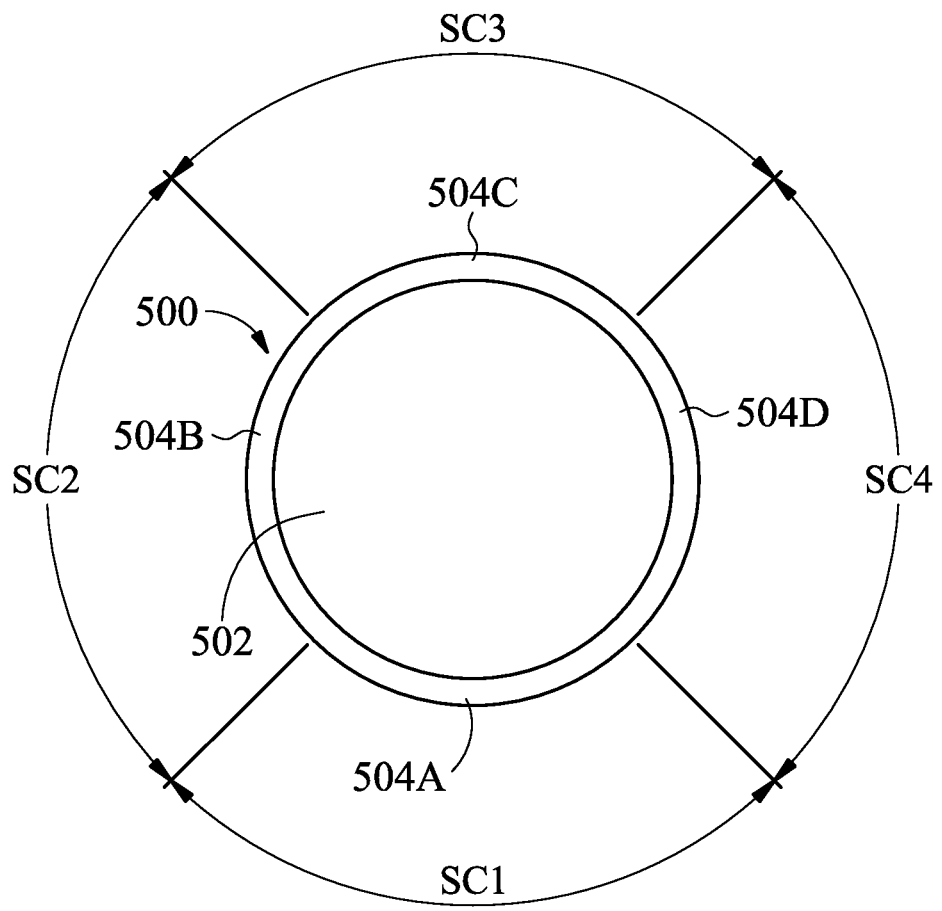
FIG. 9 shows a top view of a penis of the patient according to some embodiments of the disclosure.
Figure 10:
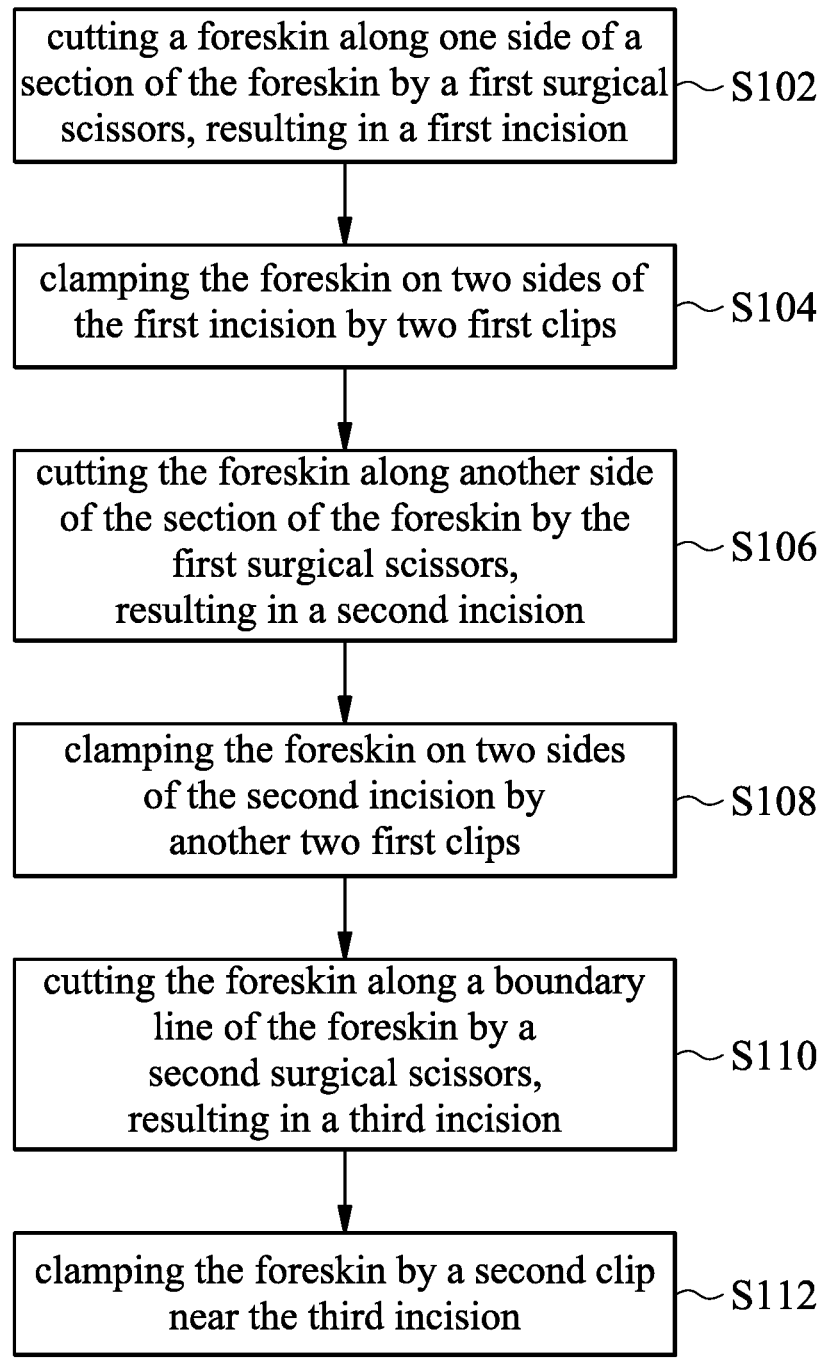
FIG. 10 is a flow chart of a circumcision method S100 according to some embodiments of the present disclosure.

Please refer to FIG. 9, FIG. 10 and FIG. 10A to FIG. 10D. FIG. 9 shows a top view of a penis 500 of the patient according to some embodiments of the disclosure. FIG. 10 is a flow chart of a circumcision method S100 according to some embodiments of the present disclosure, and FIG. 10A to FIG. 10D show diagrams illustrating the procedure of circumcision according to some embodiments of the disclosure. As shown in FIG. 9, the glans 502 is surrounded by the foreskin 504, and the foreskin 504 can be defined into four sections SC1~SC4, and the area of each of the sections SC1~SC4 is substantially the same.

Figure 10A:
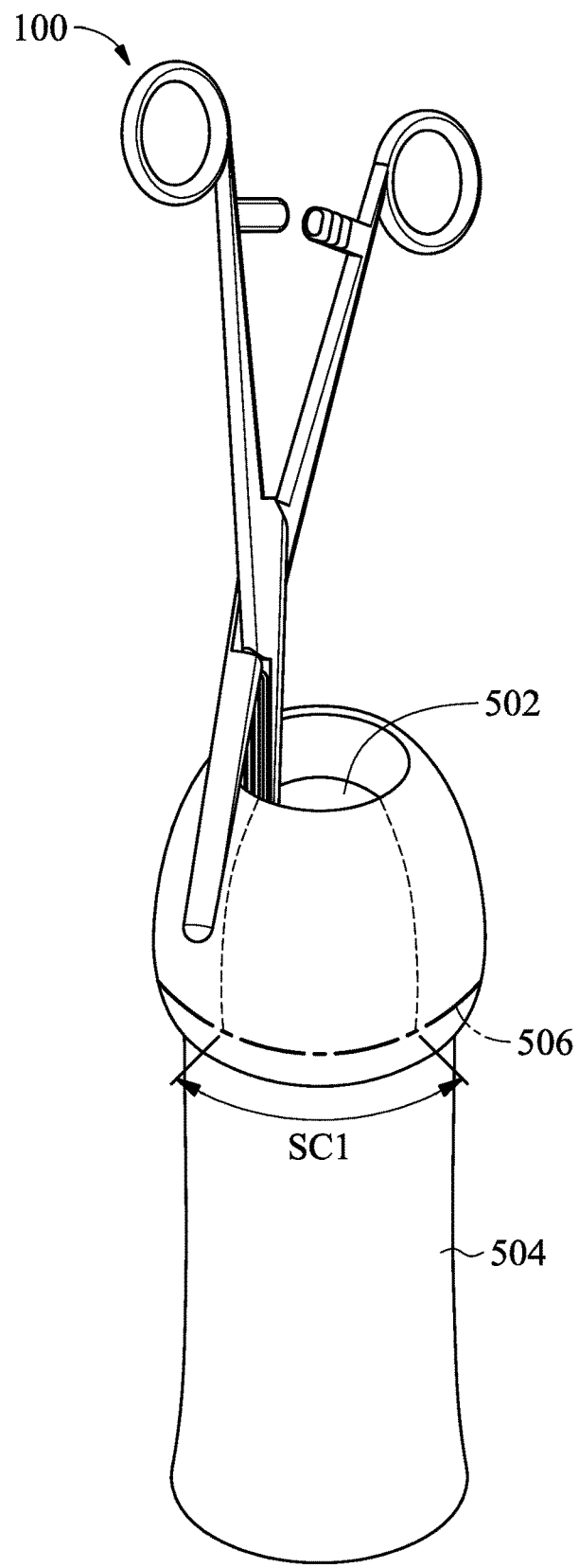
FIG. 10A to FIG. 10D show diagrams illustrating the procedure of circumcision according to some embodiments of the disclosure.
Figure 10B:
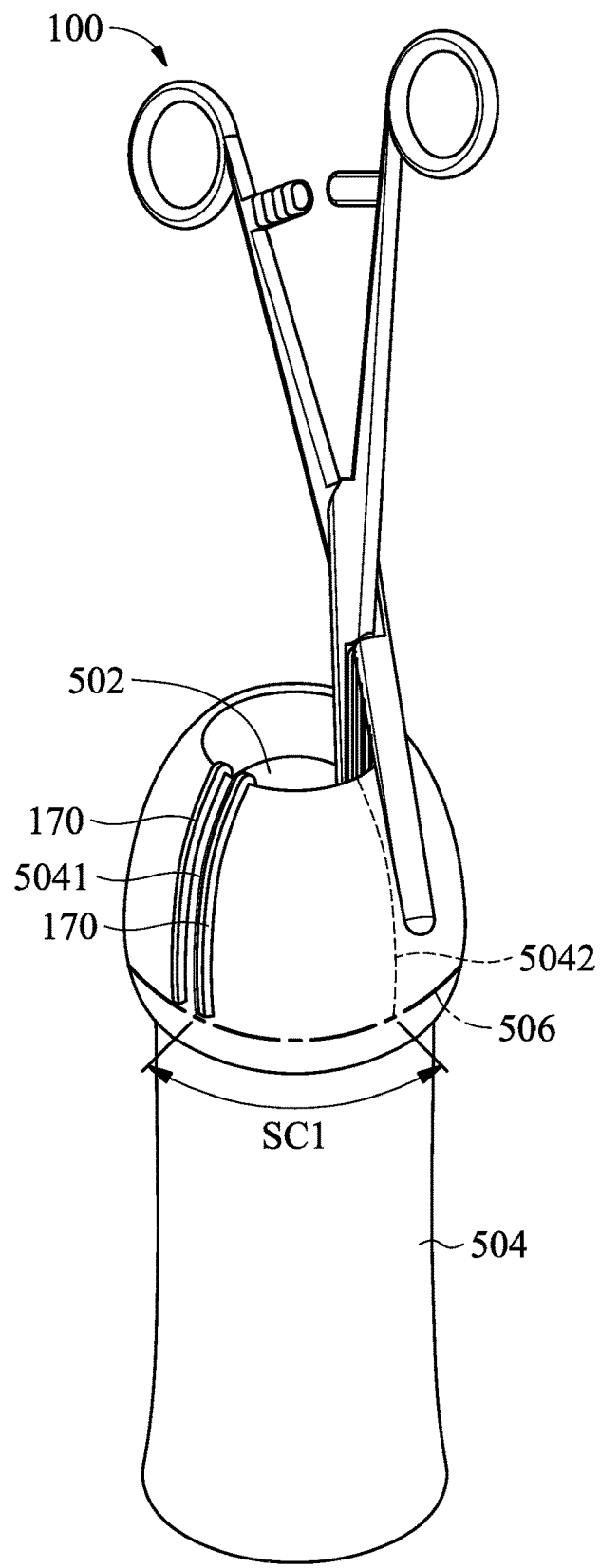

As shown in FIG. 10 and FIG. 10A to FIG. 10D, the figures illustrate that the surgeon trims the section SC1 of the foreskin 504. At first, the surgeon can mark a boundary line 506 on the foreskin 504. In step S102, the surgeon uses the first surgical scissors 100 to cut the foreskin 504 along one side of the section SC1 resulting in a first incision, as shown in FIG. 10A. As shown in FIG. 10B, the first incision (the incision 5041) stops at the boundary line 506. In step S104, when the first surgical scissors 100 cuts the foreskin 504 in step S102, the clips 170 clamp two sides of the foreskin 504 on two sides of the incision 5041. After the first surgical scissors 100 is removed, the two clips 170 still clamp the foreskin 504 on two sides of the incision 5041, so as to reduce bleeding from the incision 5041.

Then, in step S106, the surgeon continues to use the first surgical scissors 100 (or another first surgical scissors 100) to trim the foreskin 504 along the other side of the section SC1, resulting in a second incision (the incision 5042). In step S108, when the first surgical scissors 100 cuts the foreskin 504 in step S106, another two clips 170 clamps two sides of the foreskin 504 on two sides of the incision 5042. Similarly, as shown in FIG. 10C, after the first surgical scissors 100 is removed, another two clips 170 still clamp the foreskin 504 on two sides of the incision 5042, so as to reduce bleeding from the incision 5042.

Figure 10C:
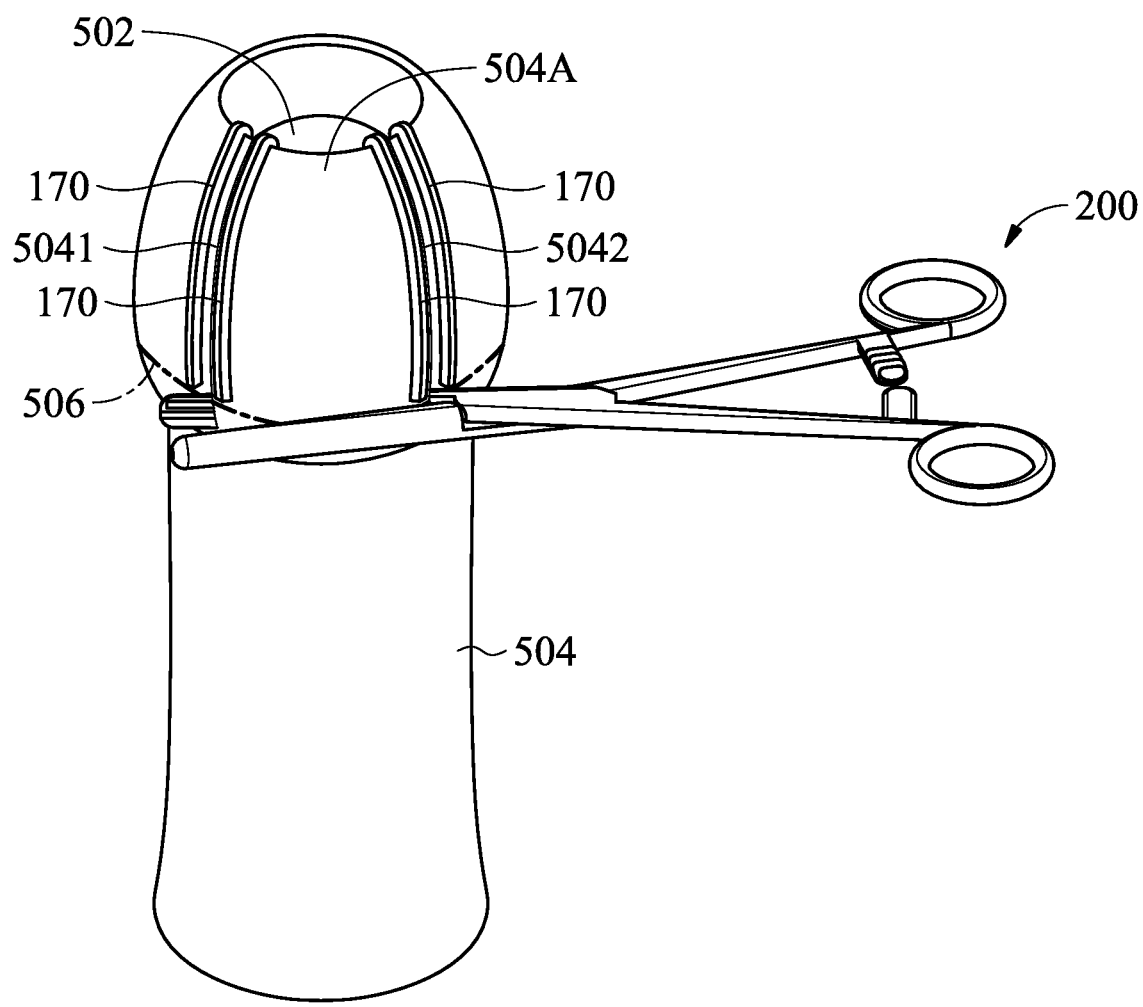
Figure 10D:
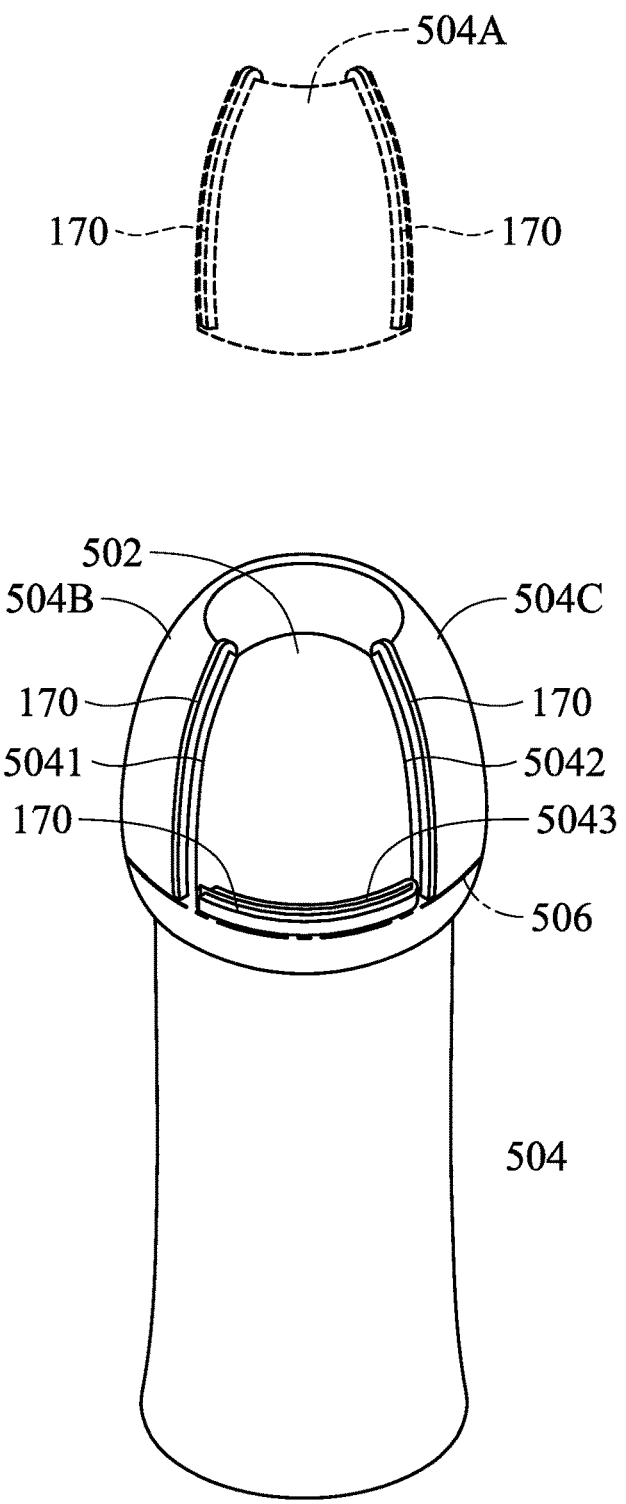

Next, please refer to FIG. 10C and FIG. 10D. After the steps in FIG. 10A and FIG. 10B, in step S110, the surgeon can pull up one piece 504A of the foreskin 504 and use the second surgical scissors 200 to cut the foreskin 504 along the boundary line 506, as shown in FIG. 10C. In step S112, when the second surgical scissors 200 cuts the foreskin 504 in step S110, the second clip (the clip 170) clamps the foreskin 504 near the incision 5043. As a result, as shown in FIG. 10D, the piece 504A of the foreskin 504 is removed, and the clip 170 of the second surgical scissors 200 remains on the foreskin 504 to clamp the foreskin 504 near a third incision (the incision 5043), so as to reduce bleeding from the incision 5043.

In addition, for example, after step S102 and before step S106, when the clips 170 on the first surgical scissors 100 are ran out, the surgeon can move the first surgical scissors 100 to the clip holder 300 to refill other clips 170 as shown in FIG. 4 and FIG. 5, so that other clips 170 can be engaged on the first surgical scissors 100.

After finishing the procedure of trimming the section SC1 of the foreskin 504, the surgeon can continue to repeat the above steps to trim the sections SC2~SC4, and therefore the pieces 504B-504D (as shown in FIG. 9) corresponding to sections SC2~SC4 are also removed, so as to complete the circumcision surgery. It should be noted that the clips 170 that remain on the pieces 504B-504D are also removed when removing the pieces 504B-504D, and only the clips 170 near the boundary line 506 remain on the foreskin 504. As a result, the clips 170 still clamp the portion of the foreskin 504 near the boundary line 506 after the surgery. After a period of time, such as one week or two weeks, the portions of the foreskin 504 which are clamped by the clips 170 will result in ischemic necrosis, and the portion of the foreskin 504 is separated from other live portions of the foreskin 504 with the clips 170.

Figure 11:
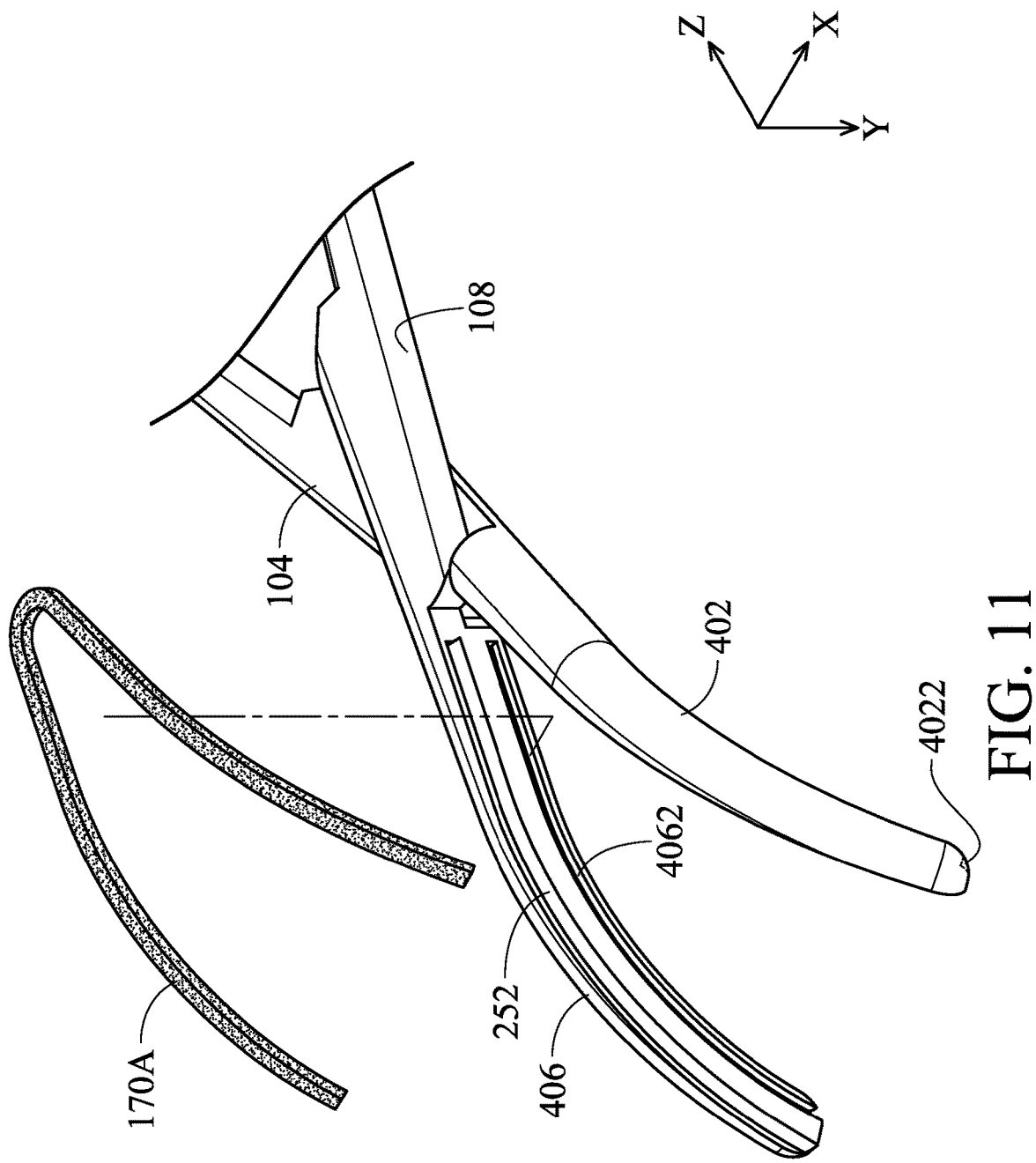
FIG. 11 shows a pair of third surgical scissors according to another embodiment of the disclosure.

Please refer to FIG. 11, which shows a third surgical scissors 400 and a curved clip 170A according to another embodiment of the disclosure. The third surgical scissors 400 are similar to the second surgical scissors 200, and the difference between the second surgical scissors 200 and the third surgical scissors 400 is that the third surgical scissors 400 include a curved scissoring portion 402 on which the long-strip groove 4022 is formed and a curved scissoring portion 406 on which the long-strip groove 4062 is formed, and the curved clip 170A is detachably installed in the long-strip groove 4062 of the curved scissoring portion 406 and the long-strip groove 4022 of the curved scissoring portion 402. The curved clip 170A has a curved-shaped structure corresponding to the two grooves 4022 and 4062.

The curvature of the curved scissoring portion 402 and the curvature of the curved scissoring portion 406 are the same, and the curvature of the curved scissoring portion 406 corresponds to the curvatures of the sections SC1~SC4 in FIG. 9. For example, the surgeon can use the third surgical scissors 400 to replace the second surgical scissors 200 in the step of FIG. 10C, so that the piece 504A can be cut more smoothly, and the incision 5043 is trimmed to be straighter. As a result, the incision of the foreskin 504 will heal faster.

Figure 12:
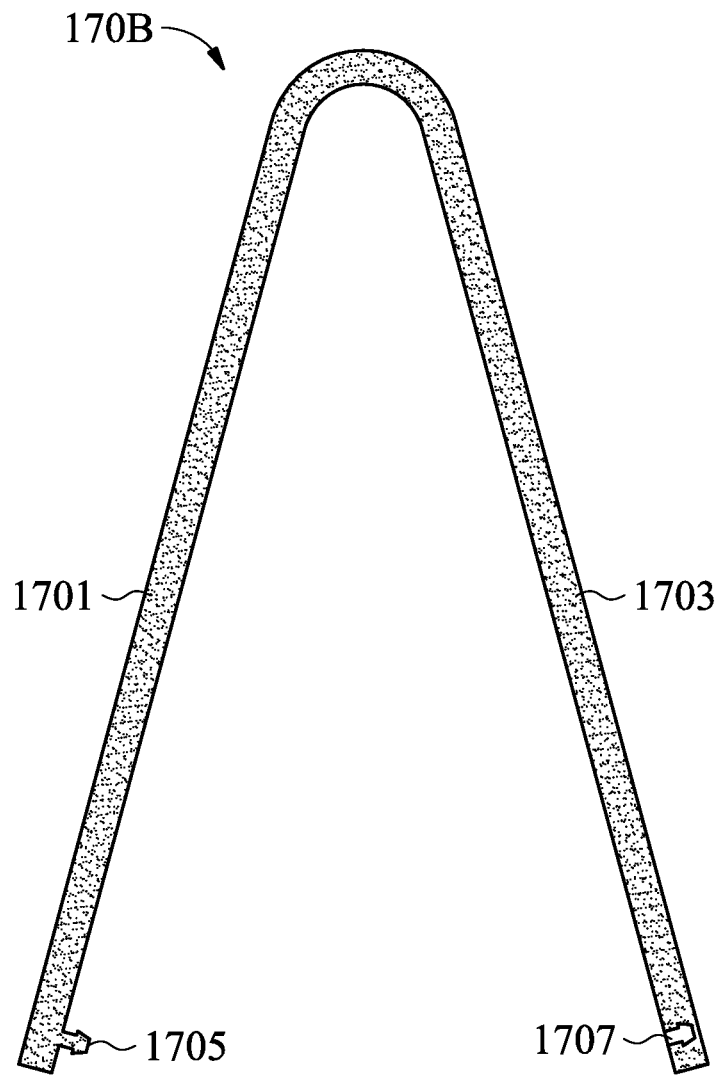
FIG. 12 shows a clip according to some embodiments of the disclosure.

Please refer to FIG. 12, which shows a clip 170B according to some embodiments of the disclosure. The clip 170B is similar to the clip 170, and the clip 170 can be replaced by the clip 170B in the previous steps in the circumcision surgery. As shown in FIG. 12, the clip 170B includes a first portion 1071 and a second portion 1703. A protrusion 1705 is formed on an end of the first portion 1071, and a slot 1707 is formed on an end of the second portion 1703. The shape of the protrusion 1705 matches the shape of the slot 1707. As a result, when the curved clip 170B is forced closed by surgical scissors, the protrusion 1705 is securely engaged with the slot 1707, so that the foreskin 504 can be tightly clamped. It should be noted that the shapes of the protrusion 1705 and the slot 1707 are not limited in this embodiment, any structure that facilitates the clip 170B to be tightly closed is within the scope of the present disclosure.

Figure 13:
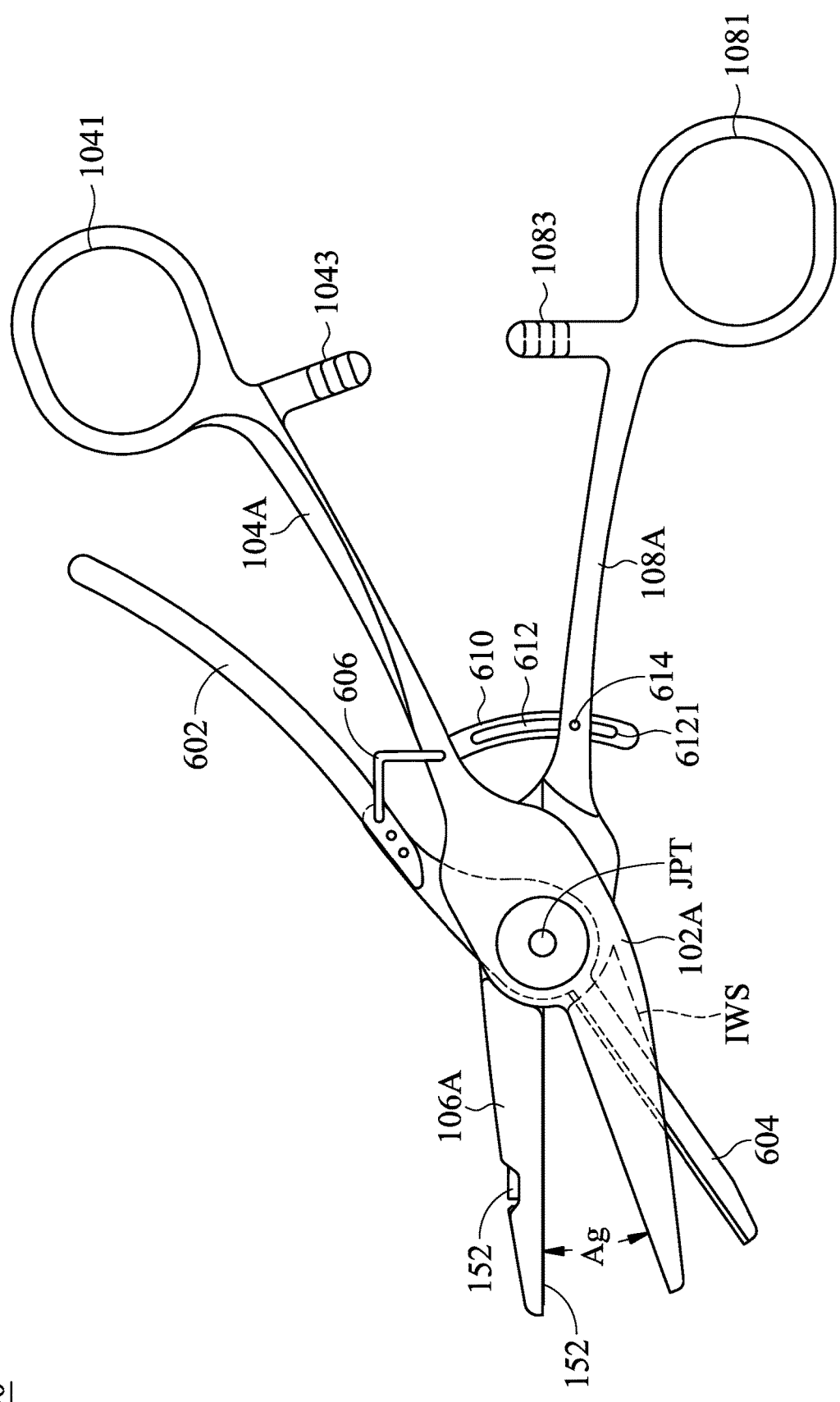
FIG. 13 shows a top view diagram of a pair of surgical scissors according to some embodiments of the present disclosure.
Figure 14:
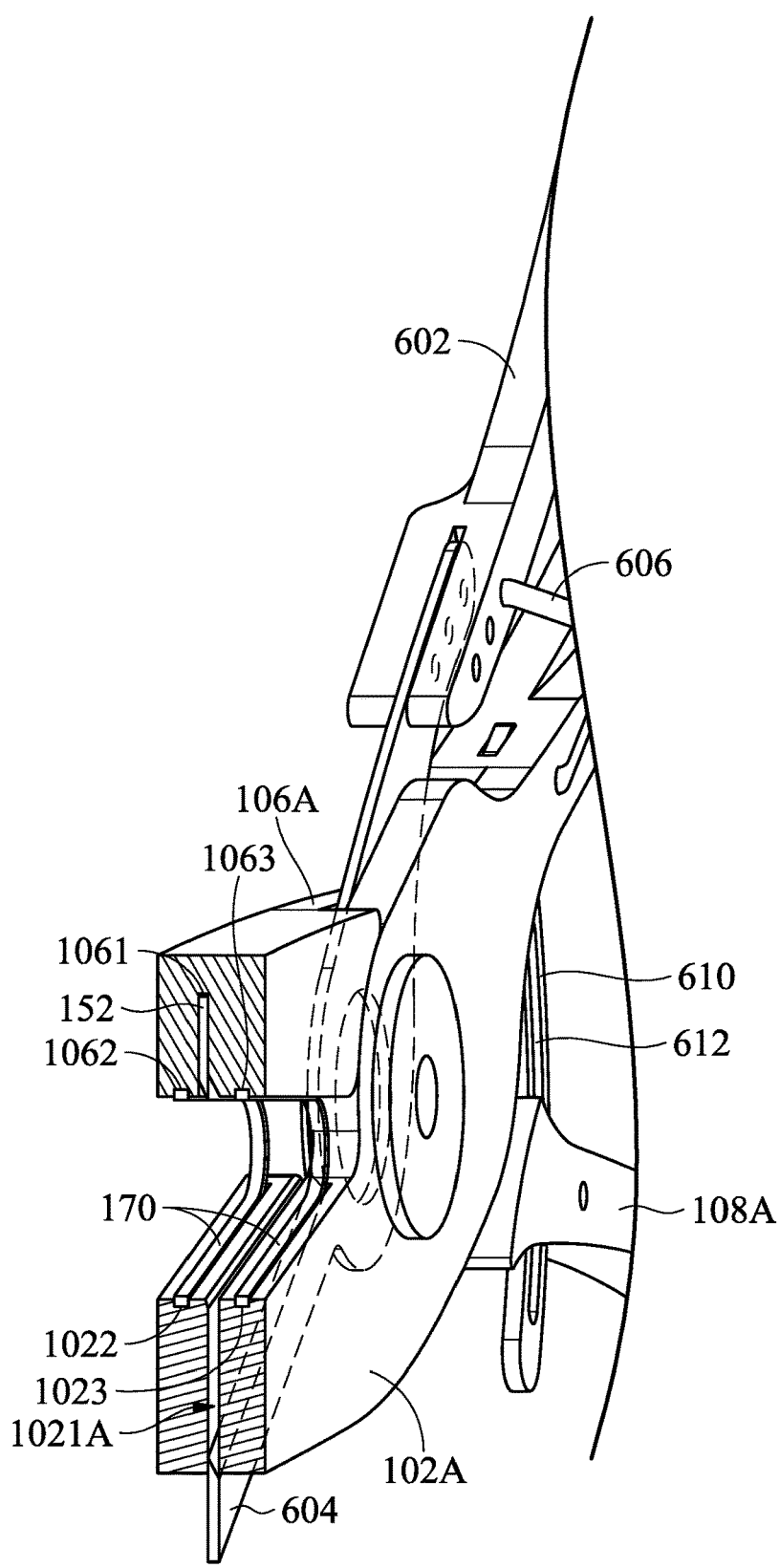
FIG. 14 shows a cross-sectional diagram of the pair of surgical scissors according to the embodiment of the present disclosure.

Please refer to FIG. 13 and FIG. 14. FIG. 13 shows a top view diagram of a pair of surgical scissors 600 according to some embodiments of the present disclosure. FIG. 14 shows a cross-sectional diagram of the pair of surgical scissors 600 according to the embodiment of the present disclosure. As shown in FIG. 13, the surgical scissors 600 include a left part, a middle part, and a right part, and the left part, the middle part and the right part are joined on a middle point JPT. In this embodiment, the middle part is sandwiched between the left part and the right part, and the middle part can rotate around the middle point JPT relative to the right part and the left part.

In this embodiment, the left part, the middle part and the right part are made of stainless steel, but they are not limited thereto. The left part includes a scissoring portion 102A and a handle portion 104A, and the right part includes a scissoring portion 106A and a handle portion 108A. The structures of the handle portion 104A and the handle portion 108A are similar to the handle portion 104 and the handle portion 108 in previous embodiments, and therefore a detailed description of the structures is omitted herein. The difference is that the surgical scissors 600 further include a guiding part 610 which is connected between the handle portion 104A and the handle portion 108A.

In this embodiment, one end of the guiding part 610 is affixed to the handle portion 104A (such as by a screw or a pin), and the guiding part 610 includes a guiding slot 612. The handle portion 108A can include a pin 614 disposed inside the guiding slot 612, so that the handle portion 108A can move along the guiding slot 612 relative to the handle portion 104A. In addition, an included angle Ag between the scissoring portion 106A and the scissoring portion 102A can be restrained by the guiding slot 612. For example, the guiding slot 612 has an end point 6121, and the included angle Ag has a maximum value when the pin 614 on the handle portion 108A reaches the end point 6121. Furthermore, when the handle portion 104A and the handle portion 108A are forced to be close to each other, the included angle Ag is about 0 degrees.

Next, please refer to FIG. 13 and FIG. 14 together. As shown in FIG. 14, there are three long-strip grooves 1061, 1062 and 1063 formed on the scissoring portion 106A, and there are one gap 1021A and two side grooves (the two long-strip grooves 1022 and 1023) formed on the scissoring portion 102A. The gap 1021A is disposed between the two long-strip grooves 1022 and 1023. The long-strip grooves 1022 and 1062 are configured to receive a clip 170, and the long-strip grooves 1023 and 1063 are configured to receive another clip 170. In addition, the long-strip groove 1061 is configured to accommodate a blade 152, and the blade 152 can be detachably installed in the long-strip groove 1061 in this embodiment, but it is not limited thereto. Moreover, as shown in FIG. 13 and FIG. 14, the middle part includes a handle portion 602 and a first blade (a blade portion 604) which are affixed to each other. When the handle portion 602 is forced, the blade portion 604 can move along the gap 1021A.

As shown in FIG. 13, the surgical scissors 600 further include a resilient member 606 which is connected to the handle portion 602 and the handle portion 104A. The resilient member 606 is configured to provide a resilient force to drive the handle portion 602 away from the handle portion 104A, and the blade portion 604 is constrained when the blade portion 604 is in contact with an inner wall surface IWS of the scissoring portion 102A.

Figure 15:
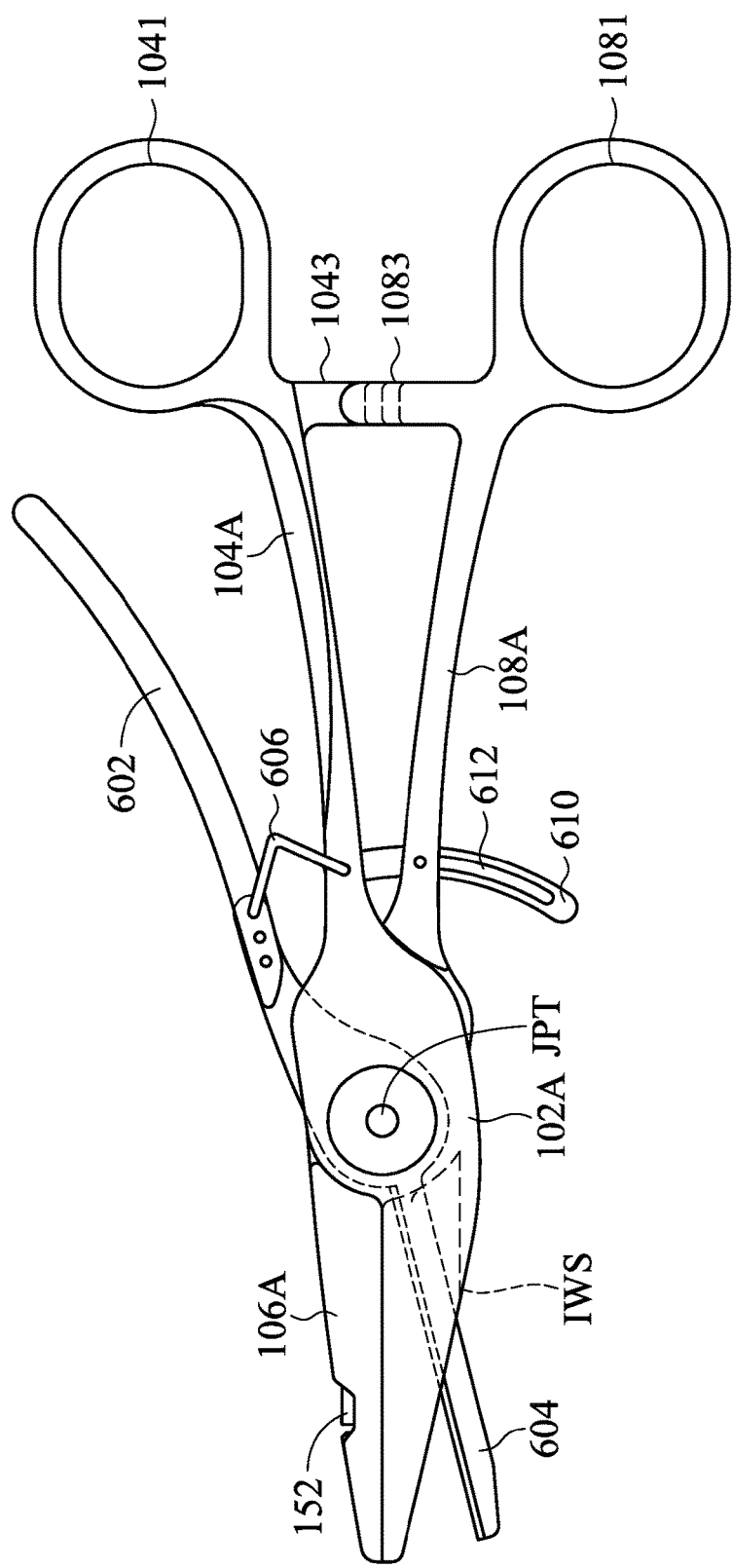
FIG. 15 illustrates that the scissoring portion and the scissoring portion are close to each other according to the embodiment of the disclosure.
Figure 16:
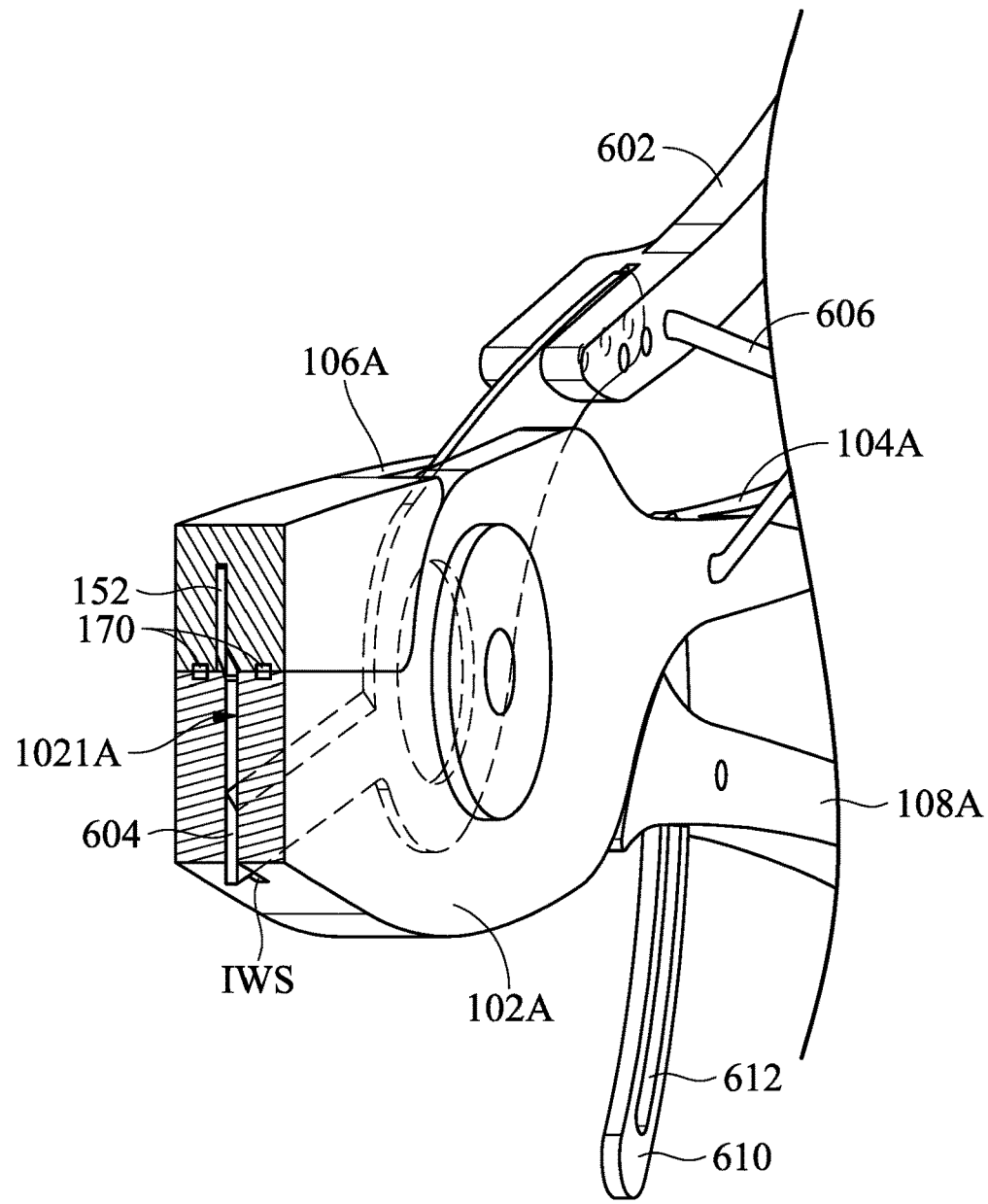
FIG. 16 shows a cross-sectional diagram of the pair of surgical scissors in FIG. 15 according to the embodiment of the present disclosure.

Please refer to FIG. 15 and FIG. 16. FIG. 15 illustrates that the scissoring portion 106A and the scissoring portion 102A are close to each other according to the embodiment of the disclosure. FIG. 16 shows a cross-sectional diagram of the pair of surgical scissors 600 in FIG. 15 according to the embodiment of the present disclosure. When the surgeon uses the surgical scissors 600 to cut a foreskin, he (or she) may force the handle portion 104A and the handle portion 108A to move toward each other, so that the scissoring portion 106A and the scissoring portion 102A are close to each other as well. Then, as shown in FIG. 16, the scissoring portion 106A is in contact with the scissoring portion 102A, and the two clips 170 clamp the foreskin (not shown in the figure). It should be noted that the foreskin is not cut by the blade 152 or the blade portion 604 at this time.

Figure 17:
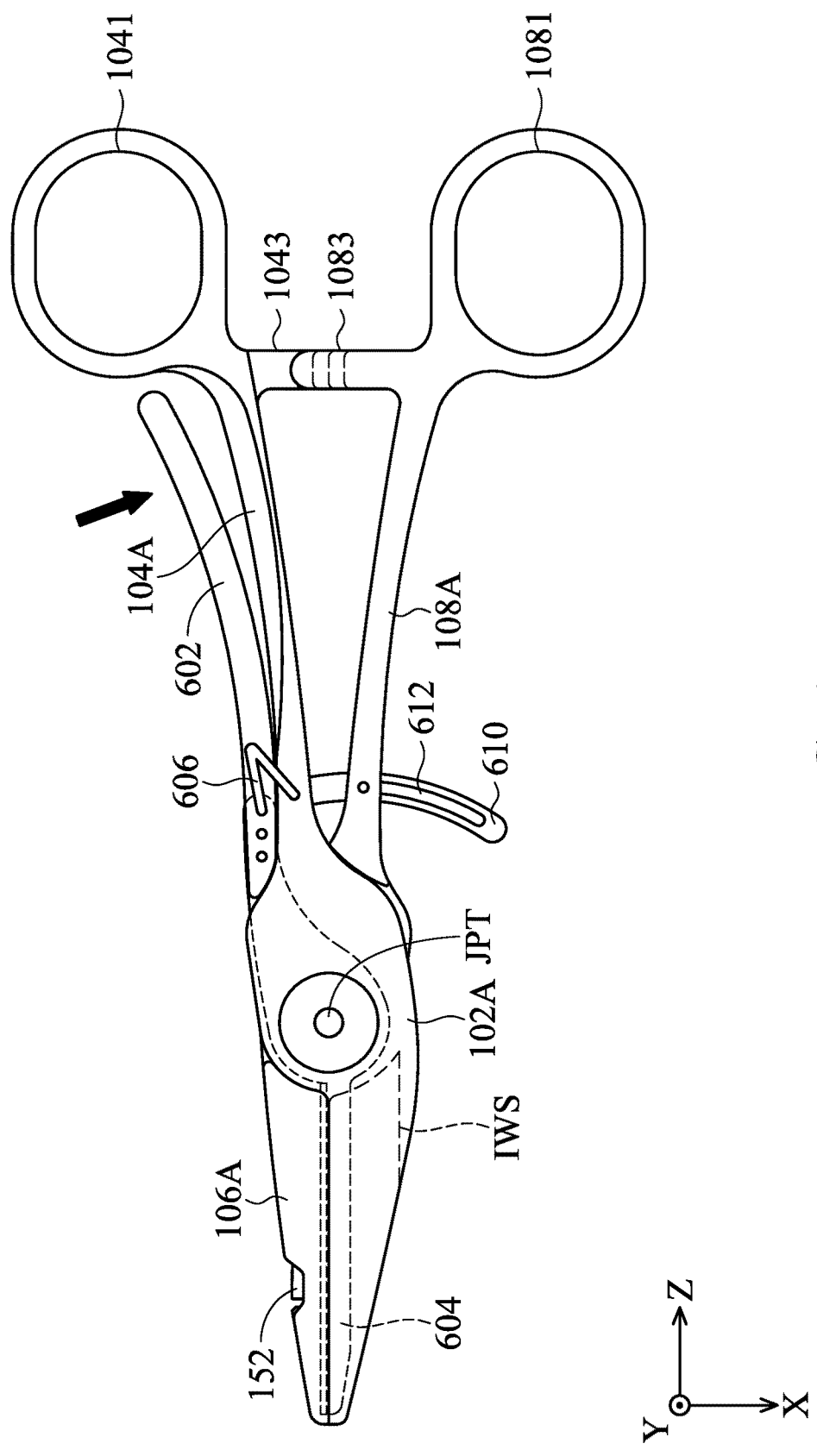
FIG. 17 illustrates that the handle portion is pushed to be close to the handle portion according to the embodiment of the disclosure.
Figure 18:
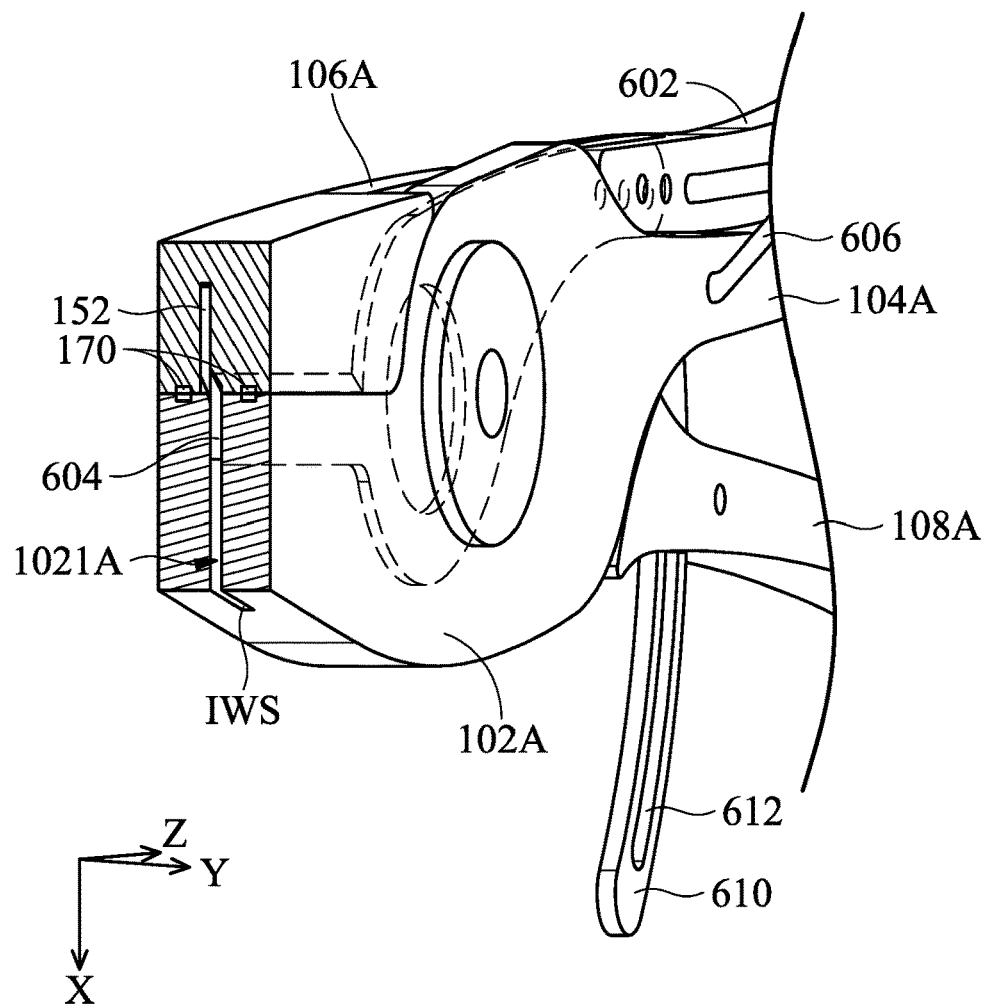
FIG. 18 shows a cross-sectional diagram of the pair of surgical scissors in FIG. 17 according to the embodiment of the present disclosure.

Please refer to FIG. 17 and FIG. 18. FIG. 17 illustrates that the handle portion 602 is pushed to be close to the handle portion 104A according to the embodiment of the disclosure. FIG. 18 shows a cross-sectional diagram of the pair of surgical scissors 600 in FIG. 17 according to the embodiment of the present disclosure. After the step in FIG. 15, the surgeon then can push down the handle portion 602 (for example, along the direction indicated by the arrow in FIG. 17), and therefore the blade portion 604 moves to be close to the scissoring portion 106A. As shown in FIG. 18, the blade portion 604 moves along the −X-direction so that the blade portion 604 is in contact with the scissoring portion 106A, and the blade portion 604 partially overlaps the blade 152 when viewed along the Y-direction, As a result, the foreskin (not shown in the figure) can be cut by the blade 152 and the blade portion 604.

Based on the structural design of the blade 152 and the blade portion 604 in the surgical scissors 600, the foreskin can be cut more smoothly and completely by the blade 152 and the blade portion 604, resulting in a very straight incision.

Figure 19:
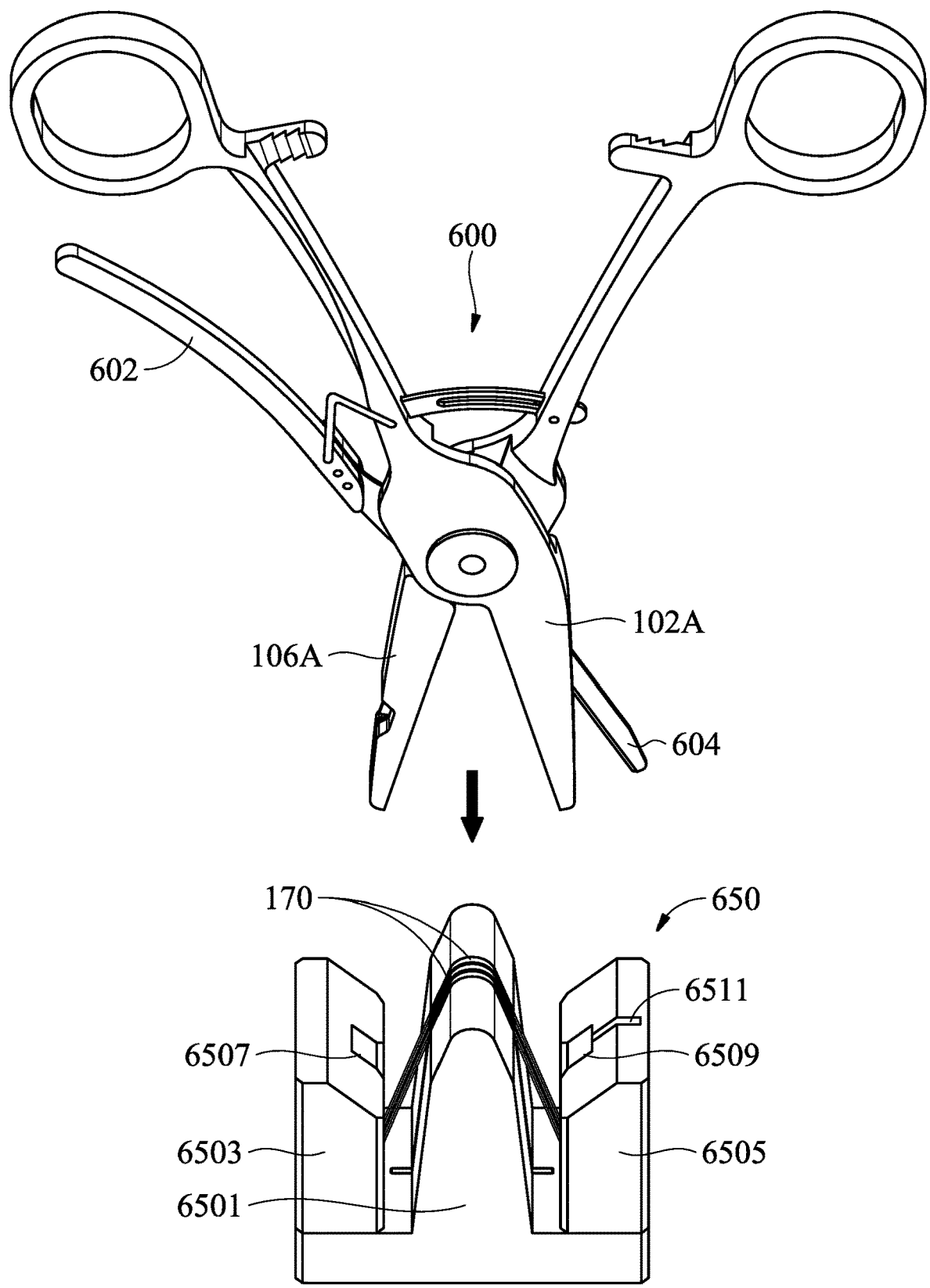
FIG. 19 shows a diagram of a clip holder and the surgical scissors according to some embodiments of the present disclosure.

Please refer to FIG. 19, which shows a schematic diagram of a clip holder 650 and the surgical scissors 600 according to some embodiments of the present disclosure. As shown in FIG. 19, the clip holder 650 includes a middle portion 6501, a side portion 6503 and a side portion 6505. The middle portion 6501 can include two grooves (not shown in the figure) to receive two clips 170, so that the two clips 170 can be stably disposed in the grooves. In this embodiment, the side portion 6503 includes a slot 6507, and the side portion 6505 includes a slot 6509. The slot 6507 and the slot 6509 are configured to respectively accommodate and constrain the scissoring portion 106A and the scissoring portion 102A.

In addition, the side portion 6505 can further include a narrow slot 6511 which is configured to receive the blade portion 604. In this embodiment, the narrow slot 6511 is communicated with the slot 6509. As shown in FIG. 19, the surgical scissors 600 can be moved toward the clip holder 650 (for example, along the direction indicated by the arrow in FIG. 19), and then the scissoring portion 106A and the scissoring portion 102A are guided by the slot 6507 and the slot 6509, so that the long strip grooves 1022, 1062, 1023 and 1063 are aligned with the two clips 170. As a result, the two clips 170 can be easily and stably accommodated in the long strip grooves 1022, 1062, 1023 and 1063.

In conclusion, the disclosure provides a circumcision apparatus, including at least one first surgical scissors 100 and at least one second surgical scissors 200. The first surgical scissors 100 includes a pair of blades and two clips, and the second surgical scissors 200 includes a pair of blades and one clip. The surgeon can use the first surgical scissors 100 to cut the foreskin 504 along the direction of the penis of the patient, and then can use the second surgical scissors 200 to remove a part of foreskin 504. Because the clips clamp the foreskin 504 before the blades cut the foreskin 504, bleeding from the incision can be effectively reduced in the procedure of the circumcision surgery.

In addition, after the surgery is finished, the clips remain on the foreskin 504. After one or two weeks, the clips and the necrotic foreskin (a small part of foreskin 504) are separated from the healthy foreskin 504 by themselves, and sutures or stitches are not required, so that the patient's daily life will not be affected. Moreover, the surgeon can use a third surgical scissors 400 instead of the second surgical scissors 200, and a part of the foreskin 504 can be cut off more smoothly. Therefore, the incision 5043 is trimmed to be straighter, and the incision of the foreskin 504 will heal faster.

Furthermore, in some embodiments, the surgeon can also use the surgical scissors 600 to perform circumcision, and the foreskin can be cut more smoothly and completely by the surgical scissors 600, resulting in a very straight incision, to help the incision of the foreskin 504 to be healed faster. Consequently, by utilizing the surgical scissors of the present disclosure mentioned above, the procedures of cutting, hemostasis and suturing can be completed at once, so as to significantly reduce operating time in contrast to the conventional circumcision operation.

Although the embodiments and their advantages have been described in detail, it should be understood that various changes, substitutions, and alterations can be made herein without departing from the spirit and scope of the embodiments as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein can be utilized according to the disclosure. Accordingly, the appended claims are intended to include within their scope such processes, machines, manufacture, compositions of matter, means, methods, or steps. In addition, each claim constitutes a separate embodiment, and the combination of various claims and embodiments are within the scope of the disclosure.

What is claimed is:

1. A circumcision apparatus, comprising:
a first surgical scissors, including:
a pair of first blades, configured to cut a foreskin along a direction of a shaft of a penis; and
two first clips, configured to clamp the foreskin near a first incision in response to the foreskin being cut by the first surgical scissors, resulting in the first incision;
wherein a height of each first clip in a first direction is greater than a height of the first blade in the first direction, so that each first clip is closer to the foreskin than the first blade.

2. The circumcision apparatus as claimed in claim 1, wherein the first surgical scissors further includes:
a left part, having:
two side grooves; and
a central groove, disposed between the side grooves of the left part; and
a right part, joined to the left part and having:
two side grooves; and
a central groove, disposed between the two side grooves of the right part;
wherein the central groove of the left part and the central groove of the right part are configured to respectively accommodate the pair of first blades, and the two side grooves of the left part and the two side grooves of the right part are configured to receive the two first clips, wherein each of the first clips has a V-shaped structure.

3. The circumcision apparatus as claimed in claim 1, wherein the circumcision apparatus further comprises a clip holder, and the clip holder has a triangular prism structure corresponding to a shape of each of the first clips.

4. The circumcision apparatus as claimed in claim 1, wherein each first clip includes:
a first portion, wherein a protrusion is formed on an end of the first portion; and
a second portion, wherein a slot is formed on an end of the second portion;
wherein a shape of the protrusion matches a shape of the slot so that the protrusion is configured to be securely engaged with the slot.

5. The circumcision apparatus as claimed in claim 1, wherein the first surgical scissors further includes:
a left part, having:
two side grooves; and
a gap, disposed between the two side grooves of the left part;
a right part, having:
two side grooves; and
a central groove, disposed between the two side grooves of the right part; and
a middle part, joined to the left part and the right part on a middle point and sandwiched between the left part and the right part, wherein the middle part is configured to rotate around the middle point relative to the right part and the left part;
wherein the two side grooves of the left part and the two side grooves of the right part are configured to receive the two first clips, the central groove of the right part is configured to accommodate one of the pair of first blades, and the middle part includes the other one of the pair of blades.

6. The circumcision apparatus as claimed in claim 5, wherein the left part further has a handle portion, the right part further has a handle portion, and the first surgical scissors further includes a guiding part which is connected between the handle portion of the left part and the handle portion of the right part.

7. The circumcision apparatus as claimed in claim 6, wherein the guiding part is affixed to the handle portion of the left part and includes a guiding slot, the handle portion of the right part includes a pin disposed inside the guiding slot, so that the handle portion of the right part is configured to move along the guiding slot relative to the handle portion of the left part.

8. The circumcision apparatus as claimed in claim 6, wherein the middle part has a handle portion, the first surgical scissors further includes a resilient member which is connected to the handle portion of the middle part and the handle portion of the left part, and the resilient member is configured to provide a resilient force to drive the handle portion of the middle part away from the handle portion of the left part.

9. The circumcision apparatus as claimed in claim 8, wherein the left part further includes a scissoring portion, and the first blade of the middle part is constrained when the first blade of the middle part is in contact with an inner wall surface of the scissoring portion of the left part.

10. The circumcision apparatus as claimed in claim 9, wherein the circumcision apparatus further comprises a clip holder, and the clip holder includes:
- a middle portion, having two grooves for receiving the two first clips; and
- two side portions, wherein each of the side portions has a slot, and the slots are configured to accommodate and constrain the left part and the right part.

11. The circumcision apparatus as claimed in claim 10, wherein one of the side portions includes a narrow slot which is configured to receive the first blade of the middle part.

12. A circumcision apparatus comprising: a surgical scissors, comprising:
- a left part, having:
- two side grooves; and
- a gap, disposed between the two side grooves of the left part;
- a right part, having:
- two side grooves; and
- a central groove, disposed between the two side grooves of the right part;
- a middle part, joined to the left part and the right part on a middle point and sandwiched between the left part and the right part, wherein the middle part is configured to rotate around the middle point relative to the right part and the left part; and
- a pair of blades, configured to cut a foreskin of a penis and two clips;

wherein the two side grooves of the left part and the two side grooves of the right part are configured to receive the two clips, the central groove of the right part is configured to accommodate one of a pair of blades, and the middle part includes the other one of the pair of blades;

wherein the blade on the central groove does not rotate relative to the right part;

wherein a height of each clip in a first direction is greater than a height of the blade on the central groove in the first direction, so that each clip is closer to the foreskin than the blade.

* * * * *